US012788981B2

(12) United States Patent
Wheeler et al.

(10) Patent No.: US 12,788,981 B2
(45) **Date of Patent: *Nov. 10, 2026**

(54) ADJUSTABLE EAR WORN APPARATUS

(71) Applicant: Aurenar, Inc., St. Louis, MO (US)

(72) Inventors: Jesse Wheeler, St. Louis, MO (US); Eric Leuthardt, St. Louis, MO (US); Jenna Gorlewicz, St. Louis, MO (US); Joe St Cyr, Hollis, NH (US); Jim Best, Hollis, NH (US); Chris Labak, Hollis, NH (US); Robert McCaffrey, Hollis, NH (US); Garrett Casey, Hollis, NH (US); Nick Vallo, Hollis, NH (US); Jay Goodell, Hollis, NH (US); Stanislav Polipas, Hollis, NH (US)

(73) Assignee: AURENAR, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/355,071

(22) Filed: Oct. 10, 2025

(65) Prior Publication Data

US 2026/0115468 A1 Apr. 30, 2026

Related U.S. Application Data

(63) Continuation-in-part of application No. 19/186,253, filed on Apr. 22, 2025, now Pat. No. 12,470,859.

(Continued)

(51) Int. Cl.

| | |
|---|---|
| ***A61N 1/36*** | (2006.01) |
| ***A61N 1/04*** | (2006.01) |
| ***H04R 1/10*** | (2006.01) |

(52) U.S. Cl.

CPC ....... *A61N 1/36036* (2017.08); *A61N 1/0456* (2013.01); *A61N 1/0472* (2013.01);

(Continued)

(58) Field of Classification Search

None

See application file for complete search history.

(56) References Cited

U.S. PATENT DOCUMENTS

| | | | | |
|---|---|---|---|---|
| 7,797,042 | B2 | 9/2010 | Dietrich et al. | |
| 8,103,040 | B2 * | 1/2012 | Pelland ............... | H04R 1/1041 381/381 |

(Continued)

FOREIGN PATENT DOCUMENTS

| | | | |
|---|---|---|---|
| AU | 2018309700 | A1 | 2/2020 |
| EP | 2129352 | A1 | 12/2009 |

(Continued)

OTHER PUBLICATIONS

John P. O'Reardon, "Vagus Nerve Stimulation (VNS) and Treatment of Depression: To the Brainstem and Beyond", Psychiatry, 2006, 10 pages.

*Primary Examiner* — Shirley X Jian

(74) *Attorney, Agent, or Firm* — Seager, Tufte & Wickhem, LLP

(57) ABSTRACT

An example wearable device for placement relative to an ear includes a housing containing electronics and a power source; a first extending structure having a first end at the housing and a second end apart from the housing, the first extending structure having a first length; a second extending structure comprising a first end at the housing and a second end apart from the housing, wherein the first and second extending structures are separated by an adjustable distance, wherein the second extending structure is configured to abut a first inner portion of an ear to create an opposing force to the first extending structure which is configured to abut a second inner portion of the ear; an anchor arm extending laterally from the first extending structure; and an adjustment mechanism configured to impart a force to adjust the adjustable distance.

30 Claims, 16 Drawing Sheets

Related U.S. Application Data

(60) Provisional application No. 63/744,537, filed on Jan. 13, 2025, provisional application No. 63/713,773, filed on Oct. 30, 2024, provisional application No. 63/698,299, filed on Sep. 24, 2024.

(52) U.S. Cl.
CPC ....... *A61N 1/36034* (2017.08); *H04R 1/1016* (2013.01); *H04R 1/1041* (2013.01); *H04R 2420/07* (2013.01)

(56) References Cited

U.S. PATENT DOCUMENTS 8,755,892 B2 6/2014 Amurthur et al.
8,965,518 B1 2/2015 Ellrich et al.
9,089,691 B2 7/2015 Libbus et al.
9,415,220 B1 8/2016 Spinelli et al.
9,987,489 B2 6/2018 Goodall et al.
10,039,928 B2 8/2018 Hyde et al.
10,293,158 B2 5/2019 Goodall et al.
10,327,984 B2 6/2019 Goodall et al.
10,398,902 B2 9/2019 Hyde et al.
10,406,376 B2 9/2019 Goodall et al.
10,426,945 B2 10/2019 Tyler et al.
10,512,783 B2 12/2019 Hyde et al.
10,537,728 B2 1/2020 Simon et al.
10,589,105 B2 3/2020 Hyde et al.
10,596,382 B2 3/2020 Goodall et al.
10,695,568 B1 6/2020 Covalin
10,695,570 B2 6/2020 Goodall et al.
10,736,564 B2 8/2020 Goodall et al.
10,806,928 B2 10/2020 Sharma et al.
10,912,712 B2 2/2021 Tracey et al.
11,103,693 B2 8/2021 Cartledge et al.
11,123,560 B1 9/2021 Nemechek
11,207,518 B2 12/2021 Huston et al.
11,351,370 B2 * 6/2022 Covalin ............. A61N 1/36028
11,364,380 B2 6/2022 Goodall et al.
11,369,791 B2 6/2022 Brown et al.
11,517,743 B2 12/2022 Chu et al.
11,612,749 B2 3/2023 Libbus et al.
11,623,088 B2 4/2023 Covalin et al.
11,684,771 B2 6/2023 Ben-David et al.
11,752,339 B2 9/2023 Connolly et al.
11,771,895 B2 10/2023 Bouton
11,813,448 B2 11/2023 Brown et al.
11,894,148 B2 2/2024 Errico et al.
12,470,859 B1 * 11/2025 Wheeler .............. H04R 1/1075
12,551,700 B2 * 2/2026 Sunkeri .............. A61N 1/36036
2009/0306454 A1 12/2009 Cockerham et al.
2011/0103636 A1 * 5/2011 Pelland .................. H04R 1/105
381/380
2012/0258132 A1 10/2012 Blumenfeld et al.
2013/0030321 A1 1/2013 Zhang
2015/0165195 A1 * 6/2015 Hartlep ................ A61N 1/3603
607/62
2015/0241447 A1 8/2015 Zitnik et al.
2018/0021217 A1 1/2018 Tracey et al.
2019/0001128 A1 1/2019 Goodall et al.
2019/0030279 A1 1/2019 Nowlin
2019/0223747 A1 7/2019 Chou
2020/0086108 A1 3/2020 Simon et al.
2020/0197707 A1 * 6/2020 Covalin ............... A61N 1/0456
2020/0238085 A1 7/2020 Khodaparast et al.
2020/0338348 A1 10/2020 Honeycutt et al.
2020/0345970 A1 11/2020 La Rovere et al.
2021/0085974 A1 * 3/2021 Bouton ................ A61B 5/4836
2021/0213286 A1 7/2021 Covalin et al.
2021/0252279 A1 8/2021 Jian
2021/0268268 A1 9/2021 Horn et al.
2021/0379374 A1 12/2021 Hamner et al.
2021/0379382 A1 12/2021 John et al.
2022/0118253 A1 4/2022 Wetmore et al.
2022/0168568 A1 6/2022 Alataris et al.
2022/0233856 A1 7/2022 Gupta et al.
2022/0233860 A1 7/2022 Hamner et al.
2022/0249840 A1 8/2022 Gupta et al.
2022/0305259 A1 9/2022 Gupta et al.
2022/0347474 A1 11/2022 Brown
2022/0370802 A1 11/2022 Tracey et al.
2023/0009158 A1 1/2023 Liberatore
2023/0026037 A1 1/2023 Larraya et al.
2023/0048804 A1 2/2023 Centanni
2023/0110411 A1 4/2023 Leuthardt et al.
2023/0145581 A1 5/2023 Sharma et al.
2023/0191126 A1 6/2023 Kent et al.
2023/0200637 A1 6/2023 Hakimimehr et al.
2023/0233855 A1 * 7/2023 Sunkeri .............. A61N 1/36036
607/55
2023/0271010 A1 8/2023 Vervoordeldonk et al.
2023/0285752 A1 9/2023 Chew et al.
2023/0302273 A1 9/2023 Ku et al.
2023/0381515 A1 11/2023 Covalin et al.
2024/0033505 A1 2/2024 Brown et al.
2024/0090821 A1 3/2024 Simon et al.
2024/0106142 A1 3/2024 Wettenstein et al.
2024/0114283 A1 * 4/2024 Wang ..................... H04R 1/105
2024/0149063 A1 * 5/2024 Leuthardt .......... A61N 1/36025
2024/0173543 A1 5/2024 Song et al.
2024/0189594 A1 * 6/2024 Hamner ............. A61N 1/36034

FOREIGN PATENT DOCUMENTS

EP 3525880 A1 8/2019
EP 3661590 A1 6/2020
EP 4243920 A1 9/2023
EP 4299107 A2 1/2024
EP 4301457 A1 1/2024
EP 4338790 A2 3/2024
GB 2604264 A 8/2022
WO 2013/165697 A1 11/2013
WO 2016/137926 A1 9/2016
WO 2021/099466 A2 5/2021
WO 2021/105744 A1 6/2021
WO 2021/263098 A1 12/2021
WO 2022/146295 A1 7/2022
WO 2022/221858 A2 10/2022
WO 2022/266063 A1 12/2022
WO 2023/283568 A1 1/2023
WO 2023/017253 A1 2/2023
WO 2023/059760 A1 4/2023
WO 2023/141609 A2 7/2023
WO 2023/224636 A1 11/2023
WO 2023/235474 A1 12/2023
WO 2024/031086 A1 2/2024
WO 2024/038263 A1 2/2024
WO 2024/086209 A2 4/2024

* cited by examiner

ADJUSTABLE EAR WORN APPARATUS

CROSS REFERENCE TO RELATED APPLICATIONS

The present application is a continuation in part of U.S. application Ser. No. 19/186,253, filed Apr. 22, 2025, which claims the benefit of and priority to U.S. Provisional Patent Application No. 63/698,299, filed Sep. 24, 2024, titled ANTI-INFLAMMATORY AURICULAR VAGAL NERVE STIMULATION, and U.S. Provisional Patent Application No. 63/713,773, filed Oct. 30, 2024, titled AURICULAR VAGAL NERVE STIMULATION TO MITIGATE INFLAMMATORY COMPLICATIONS FOR BIOACTIVE AGENTS, U.S. Provisional Patent Application No. 63/744,537, filed Jan. 13, 2025, titled WEARABLE DEVICES WITH ADJUSTMENT MECHANISMS, and U.S. patent application Ser. No. 19/186,253, filed Apr. 22, 2025, titled "ADJUSTABLE EAR WORN APPARATUS, the disclosures of which are incorporated herein by reference.

BACKGROUND

Wearable devices, particularly those designed to be disposed in or around the ear, have gained significant popularity in recent years. These devices, such as earbuds, are small, portable, and often wireless, providing users with hands-free access to audio, communication, and various smart functions. Earbuds can connect to smartphones, computers, and other devices via BLUETOOTH® or other wireless communication protocols, offering features like sound (e.g., music) delivery, noise cancellation, voice assistants, fitness tracking, etc. For instance, their compact size and comfort make them ideal for daily use, whether for listening to music, taking calls, or tracking physical activity.

Overview

Another illustrative and non-limiting example takes the form of a wearable device adapted for placement relative to an ear of a user, comprising a housing containing, electronics and a power source; wherein the housing comprises a lower container and an upper lid, a first extending structure having a first end at the housing and a second end apart from the housing, the first extending structure having a first length, the second end configured for contacting the posterior edge of the crus and/or antitragus; a first anchor arm extending laterally from the first extending structure and carrying an anchor element thereon, the anchor element configured for positioning beneath a tragus of the ear of the user to thereby support positioning of the device; a second extending structure comprising a first end at the housing and a second end apart from the housing, wherein the first and second extending structures are separated by an adjustable distance; a carriage coupled to the first end of the second extending structure and being at least partially disposed within the housing, wherein the carriage is configured to move longitudinally along a length of the housing; and an adjustment mechanism coupled to the carriage, wherein the adjustment mechanism is configured to impart a force to cause longitudinal movement of the carriage to adjust the adjustable distance.

Additionally, or alternatively, wherein the adjustment mechanism is an individual adjustment mechanism that is configured to be actuated by contact from one or more digits on an individual hand of a person.

Additionally, or alternatively, wherein: the adjustment mechanism is located at a first end of the housing; and a portion of the adjustment mechanisms extends a distance from the first end of the housing and a portion of the adjustment mechanism is located inside of the housing.

Additionally, or alternatively, wherein the second extending structure is configured to abut a first portion of an ear to create an opposing force to the first extending structure which is configured to abut a second portion of the ear, wherein the first portion of the ear is the inferior crus, the antihelix, or both, and wherein the second portion of the ear is the antitragus.

Additionally, or alternatively, wherein the adjustment mechanism is integral with the carriage.

Additionally, or alternatively, wherein the adjustment mechanism is located on a first end of the carriage, and wherein the adjustment mechanism comprises a protrusion extending radially from the carriage.

Additionally, or alternatively, wherein a speaker, a sensor, or both the speaker and the sensor are positioned on the first extending structure or the second extending structure.

Additionally, or alternatively, wherein the adjustment mechanism comprises a separate component that is coupled to the carriage.

Additionally, or alternatively, wherein adjustment mechanism comprises a lever or a wheel.

Additionally, or alternatively, wherein the adjustment mechanism further comprises a rotatable adjustment mechanism including an annulus, wherein the rotatable adjustment mechanism is configured to rotate about the annulus relative to the carriage, the housing, or both the carriage and the housing.

Additionally, or alternatively, wherein: the housing includes a slot extending through the first end of the housing; the rotatable adjustment mechanism comprises: a lever extending laterally therefrom through the slot to a position outside of the housing; and teeth disposed along at least a portion of a periphery of the rotatable adjustment mechanism that is located in the housing; and the carriage includes corresponding teeth that are configured to interface with the teeth to impart a force on the carriage to cause the longitudinal movement of the carriage responsive to rotation of the lever of the adjustment mechanism.

Additionally, or alternatively, wherein the carriage includes an elongated longitudinal slot extending along a portion of the length of the carriage; and the lower lid includes a peg configured to extend into the elongated longitudinal slot.

Additionally, or alternatively, wherein the housing includes a slot extending through the first end of the housing; and the rotatable adjustment mechanism comprises a wheel with a toothed surface along at least a portion of a periphery of the rotatable adjustment mechanism and a curvilinear slot extending within a portion of the wheel.

Another illustrative and non-limiting example takes the form of a wearable device adapted for placement relative to an ear of a user, comprising: a housing containing, electronics and a power source, the housing comprises a lower container and an upper lid defining a cavity therebetween; a first extending structure having a first end at the housing and a second end apart from the housing, the first extending structure having a first length, the second end configured for contacting the posterior edge of the crus and/or antitragus; a first anchor arm extending laterally from the first extending structure and carrying an anchor element thereon, the anchor element configured for positioning beneath a tragus of the ear of the user to thereby support positioning of the device;

a second extending structure comprising a first end at the housing and a second end apart from the housing, wherein the first and second extending structures are separated by an adjustable distance; a carriage coupled to the first end of the second extending structure and being at least partially disposed within the cavity of the housing, wherein the carriage is configured to translate longitudinally along a length of the housing; an adjustment mechanism coupled to the carriage, wherein the adjustment mechanism is an individual adjustment mechanism that is configured to impart a force to cause longitudinal translation of the carriage to adjust the adjustable distance; and a speaker positioned on the first extending structure or the second extending structure.

Additionally, or alternatively, wherein the adjustment mechanism comprises a fixed protrusion extending radially from the carriage or a rotatable adjustment mechanism coupled to an end of the carriage; or the carriage, the housing, or both the carriage and the housing include detents configured to predispose the carriage to one or more longitudinal positions along a length of travel of the carriage.

Additionally, or alternatively, wherein the first extending structure is located on a first side of the housing, a second side of the housing opposite the first side comprises at least one control button or switch for controlling activity of the electronics, and wherein the second extending structure is configured to abut a first portion of an ear to create an opposing force to the first extending structure which is configured to abut a second portion of the ear, wherein the first portion of the ear is the inferior crus, the antihelix, or both, and wherein the second portion of the ear is the antitragus.

Additionally, or alternatively, wherein a sensor is positioned on the first extending structure or the second extending structure.

Another illustrative and non-limiting example takes the form of a method of positioning a wearable device in an ear of a user, the wearable device comprising a housing and a first extending structure carrying thereon an anchor arm adapted for positioning in the auditory canal of a user, a second extending structure spaced from the first extending structure, a carriage coupled to the second extending structure, and an adjustment mechanism disposed at a first end of the housing and being configured to adjust a distance between the second extending structure and the first extending structure by imparting a force on the carriage to cause longitudinal movement of the carriage, the method comprising: placing the anchor arm in the auditory canal or at least partially beneath the tragus; and actuating the adjustment mechanisms to vary an adjustable distance between the first extending structure and the second extending structure until the second extending structure abuts the helix, the antihelix, the inferior crus, or any combination thereof.

Additionally, or alternatively, wherein actuating the adjustment mechanism further comprises actuating the adjustment mechanism subsequent to placing the anchor arm in the auditory canal or at least partially beneath the tragus.

Additionally, or alternatively, wherein the adjustment mechanism is spring loaded to expand, and actuating the adjustment mechanism further comprises compression against the expansion such that when released the spring expands to securely anchor the device between the antihelix and lower concha.

Additionally, or alternatively, further comprising actuating the adjustment mechanism with one or more digits on an individual hand of a user.

Additionally, or alternatively, wherein the carriage, the adjustment mechanism, the housing, or any combination thereof, includes detents.

Additionally, or alternatively, wherein the carriage, the housing, or both the carriage and the housing includes detents to resist or arrest movement of the carriage into one or more spaced intervals, wherein detents are one of magnetic or mechanical structures.

Additionally, or alternatively, wherein the adjustment mechanism includes detents to resist or arrest movement of the carriage into one or more spaced intervals, wherein detents are one of magnetic or mechanical structures.

Additionally, or alternatively, wherein a speaker is positioned on the first extending structure, the second extending structure, or both the first extending structure and the second extending structure.

Additionally, or alternatively, a speaker, an electrical sensor, or both a speaker and an electrical sensor is positioned on the first extending structure or the second extending structure.

Another illustrative and non-limiting example takes the form of wearable device for placement relative to an ear includes a housing containing electronics and a power source; a first extending structure having a first end at the housing and a second end apart from the housing, the first extending structure having a first length; a second extending structure comprising a first end at the housing and a second end apart from the housing, wherein the first and second extending structures are separated by an adjustable distance, wherein the second extending structure is configured to abut a first inner portion of an ear to create an opposing force to the first extending structure which is configured to abut a second inner portion of the ear; an anchor arm extending laterally from the first extending structure; and an adjustment mechanism configured to impart a force to adjust the adjustable distance.

Additionally, or alternatively, wherein the adjustment mechanism is located at a first end of the housing; and a portion of the adjustment mechanism extends a distance from the first end of the housing and a portion of the adjustment mechanism is located inside of the housing.

Additionally, or alternatively, wherein the first inner portion of the ear is the inferior crus, the antihelix, or both, and wherein the second inner portion of the ear is the antitragus.

Additionally, or alternatively, wherein the adjustment mechanism is integral with a carriage, wherein the carriage is coupled to the first end of the second extending structure and is configured to move longitudinally along a length of the housing.

Additionally, or alternatively, wherein the adjustment mechanism is located on a first end of the carriage, and wherein the adjustment mechanism comprises a protrusion extending radially from the carriage.

Additionally, or alternatively, wherein a speaker, a sensor, or both the speaker and the sensor are positioned on the first extending structure or the second extending structure.

Additionally, or alternatively, wherein the adjustment mechanism comprises a separate component that is coupled to a carriage, wherein the carriage is coupled to the first end of the second extending structure and is configured to move longitudinally along a length of the housing.

Additionally, or alternatively, wherein the adjustment mechanism further comprises a rotatable adjustment mechanism including an annulus, wherein the rotatable adjustment mechanism is configured to rotate about the annulus relative to the carriage, the housing, or both the carriage and the housing.

Additionally, or alternatively, the housing includes a slot extending through the first end of the housing; the rotatable adjustment mechanism comprises: a lever extending laterally therefrom through the slot to a position outside of the housing; and teeth disposed along at least a portion of a periphery of the rotatable adjustment mechanism that is located in the housing; and the carriage includes corresponding teeth that are configured to interface with the teeth to impart the longitudinal movement of the carriage responsive to rotation of the lever.

Additionally, or alternatively, wherein: the carriage includes an elongated longitudinal slot extending along a portion of the length of the carriage; and the housing includes a peg configured to extend into the elongated longitudinal slot.

Additionally, or alternatively, wherein: the housing includes a slot extending through the first end of the housing; and the rotatable adjustment mechanism comprises a wheel with a toothed surface along at least a portion of a periphery of the rotatable adjustment mechanism and a curvilinear slot extending within a portion of the wheel.

Additionally, or alternatively, wherein an electrode is positioned on the first extending structure or the second extending structure.

Additionally, or alternatively, wherein a first electrode is positioned on the first extending structure and a second electrode is positioned on the second extending structure.

Additionally, or alternatively, wherein: the first electrode and the second electrode are configured to be positioned on opposing sides of the crus helix; or the first electrode is configured to be positioned at the conchae caverna and the second electrode is configured to be positioned at the conchae cymba.

Another illustrative and non-limiting example takes the form of a wearable device adapted for placement relative to an ear of a user, comprising: a housing containing, electronics and a power source, wherein the housing comprises a lower container and an upper lid defining a cavity therebetween; a first extending structure having a first end at the housing and a second end apart from the housing, the first extending structure having a first length; an anchor arm extending laterally from the first extending structure; a second extending structure comprising a first end at the housing and a second end apart from the housing, wherein the first and second extending structures are separated by an adjustable distance, wherein the second extending structure is configured to abut a first inner portion of an ear to create an opposing force to the first extending structure which is configured to abut a second inner portion of the ear; a carriage coupled to the first end of the second extending structure and being at least partially disposed within the cavity of the housing, wherein the carriage is configured to translate longitudinally along a portion of a length of the housing; an adjustment mechanism coupled to the carriage, wherein the adjustment mechanism is an individual adjustment mechanism that is configured to impart a force to cause longitudinal translation of the carriage to adjust the adjustable distance; and an electrode, a vibrating element, or both, wherein the electrode, the vibrating element or both, is positioned on the first extending structure, the second extending structure, or both the first extending structure and the second extending structure.

Additionally, or alternatively, wherein: the adjustment mechanism comprises a fixed protrusion extending radially from the carriage or a rotatable adjustment mechanism coupled to an end of the carriage; or the carriage, the housing, or both the carriage and the housing include detents configured to predispose the carriage to one or more longitudinal positions along a length of travel of the carriage.

Additionally, or alternatively, wherein the first extending structure or the second extending structure is integral with the housing.

Additionally, or alternatively, wherein: the first inner portion of the ear is the inferior crus, the antihelix, or both, and wherein the second inner portion of the ear is the antitragus; the wearable device includes the electrode, and the electrode includes a first electrode is positioned on the first extending structure and a second electrode is positioned on the second extending structure.

Additionally, or alternatively, wherein the electronics comprise wireless communication circuitry configured to wirelessly communicate with a mobile device application, wherein the mobile device application is configured to remotely control electrical stimulation parameters delivered via the electrode, the vibrating element, or both, and wherein the wireless communication circuitry comprises BLUETOOTH® or WIFI® communication capability.

Another illustrative and non-limiting example takes the form of a method of treating inflammation in a patient, the method comprising: applying a wearable device to an ear of the patient, the wearable device comprising a housing containing electronics, one or more electrodes, and a power source, a first extending structure having a second end positioned within the ear when the wearable device is worn, an anchor arm extending laterally from the first extending structure, a second extending structure having a second end positioned within the ear when the wearable device is worn, a carriage coupled to a first end of the second extending structure and being at least partially disposed within the housing, wherein the carriage is configured to move longitudinally along a length of the housing, and an adjustment mechanism coupled to the carriage, wherein the adjustment mechanism is configured to impart a force to cause longitudinal movement of the carriage to adjust a distance between the first extending structure and the second extending structure; and delivering electrical stimulation via the one or more electrodes of the wearable device to activate a neuroimmune anti-inflammatory pathway in the patient to treat the inflammation.

Additionally, or alternatively, wherein the applying further comprises: placing the anchor arm in the ear of the user; and actuating the adjustment mechanism to vary an adjustable distance between the first extending structure and the second extending structure.

Additionally, or alternatively, wherein actuating the adjustment mechanism further comprises actuating the adjustment mechanism with one or more digits of an individual hand of a user subsequent to placing the anchor arm in the ear of the user until the second extending structure abuts the helix, the antihelix, the inferior crus, or any combination thereof.

Additionally, or alternatively, further comprising delivering the electrical stimulation at a current amplitude in a range of about 0.1 mA to about 20 mA, a pulse width in a range of about 10 microseconds to about 20 milliseconds, and a frequency in a range of about 1 Hz to about 200 Hz.

Additionally, or alternatively, wherein the inflammation is associated with one or more conditions selected from the group consisting of: cerebrovascular disorders including stroke and post-stroke inflammatory response; metabolic disorders including diabetes mellitus and glycemic control disorders; drug-induced inflammatory responses including diabetes drug therapy complications; rheumatoid arthritis; inflammatory bowel disease; Alzheimer's disease, Crohn's disease; ulcerative colitis; multiple sclerosis; psoriatic arthritis; osteoarthritis; psoriasis; chronic inflammatory symptoms; and chronic fatigue syndrome.

Another illustrative and non-limiting example takes the form of a wearable device adapted for placement relative to an ear of a user, comprising: a housing containing electronics and a power source; a first extending structure having a first end at the housing and a second end apart from the housing, the first extending structure having a first length, the second end configured for contacting the posterior edge of the crus and/or antitragus; a first anchor arm extending laterally from the first extending structure and carrying an anchor element thereon, the anchor element configured for positioning beneath a tragus of the ear of the user to thereby support positioning of the wearable device; a second extending structure comprising a first end at the housing and a second end apart from the housing, wherein the first and second extending structures are separated by an adjustable distance; a carriage coupled to the first end of the second extending structure and being at least partially disposed within the housing, wherein the carriage is configured to move longitudinally along a length of the housing; an adjustment mechanism coupled to the carriage, wherein the adjustment mechanism is configured to impart a force to cause longitudinal movement of the carriage to adjust the adjustable distance; and; an electrode, a vibrating element, or both, wherein the electrode, the vibrating element, or both, is located on the first extending structure, the second extending structure, or both.

Additionally, or alternatively, wherein the wearable device is configured to treat inflammation in the user.

Additionally, or alternatively, wherein the inflammation is associated with one or more conditions selected from the group consisting of: cerebrovascular disorders including stroke and post-stroke inflammatory response; metabolic disorders including diabetes mellitus and glycemic control disorders; drug-induced inflammatory responses including diabetes drug therapy complications; rheumatoid arthritis; inflammatory bowel disease; Alzheimer's disease, Crohn's disease; ulcerative colitis; multiple sclerosis; psoriatic arthritis; osteoarthritis; psoriasis; chronic inflammatory symptoms; and chronic fatigue syndrome.

Additionally, or alternatively, including the electrode on the first extending structure, the second extending structure, or both.

Additionally, or alternatively, including the vibrating element on the first extending structure, the second extending structure, or both.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

The drawings illustrate, by way of example, but not by way of limitation, various embodiments discussed herein. In the drawings, which are not necessarily drawn to scale, like numerals may describe similar components in different views.

DETAILED DESCRIPTION

Figure 1:
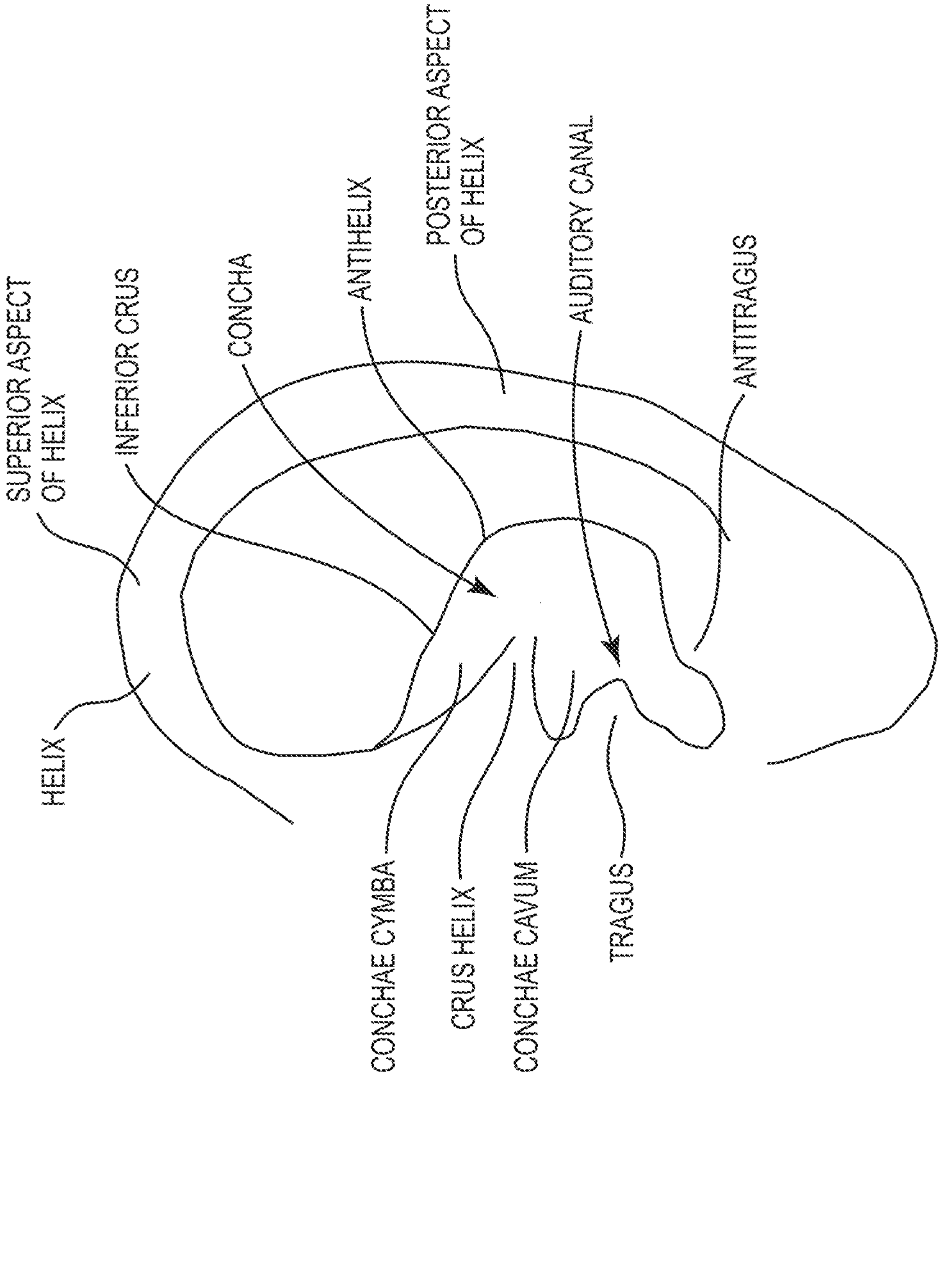
FIG. 1 is a sketch of the human ear.

FIG. 1 is a sketch of the human ear. The auditory canal is covered at its opening by the tragus, and opens adjacent the concha. The concha is typically bisected by the crus helix into the conchae cymba superiorly and conchae cavum inferiorly. The helix is the outer rim of the ear that extends from the superior insertion of the ear on the scalp to the termination of the cartilage at the earlobe, having a superior aspect and posterior aspect, as marked in the drawing. The border of the helix usually forms a rolled rim, but the helix is highly variable in shape. The crus helix is the continuation of the anteroinferior ascending portion of the helix, and as shown in the drawing, extends in a posteroinferior direction into the cavity of the concha, typically about one half to two thirds the distance across the concha. The concha is generally bordered by the antihelix superiorly and antitragus inferiorly.

The aim in some examples herein is to provide a wearable device which is compact and non-intrusive, being easily placed and operated for a user. Some examples may have an intended life of up to two weeks or longer, after which the device is intended to be discarded. Alternatively, the device can be discarded after each individual use. Other examples may provide such a wearable device, but for use at home or in other contexts and for different time durations. Some examples are characterized by having the anchoring devices are all in a single housing, which may include a clip or may be used with adhesive tape for securing the apparatus in place.

Moreover, in some embodiments, the system and/or device herein may be provided with an audio output device (e.g., a transducer or speaker). For example, the transducer or other type of audio output element can be positioned in one or both of the extending structures described herein. Hence, in some embodiments an audio output device such as a speaker can be positioned on the first extending structure or the second extending structure. A circuit board, as described herein, can be configured to operate (e.g., turn on/off, alter volume, etc.) the transducer or other type of audio output element. For instance, the system/device herein may be manifested as an auditory ear bud including a transducer (with or without a sensor/stimulator element), such as a speaker.

While some figures herein are described as having electrodes as vagus nerve stimulation elements for purpose of delivering therapy to a user or patient, other devices, methods and/or modalities can be used. Examples may use any of optical stimulation with light sources (optical transducers) such as lasers (including vertical cavity emitting lasers) or light emitting diodes including, for example and without limitation, optical stimulation using wavelengths in the infrared, near-infrared, and/or visible spectrum. Other examples may use vibratory or acoustic stimulation with frequencies from relatively low levels (tens to hundreds of hertz) up to ultrasound frequency. Such stimulation may be described as mechanical stimulation, and may use a mechanical transducer to convert electrical energy to acoustic/vibratory energy using, for example a speaker or ultrasound generator. Some examples may use magnetic stimulation with electromagnetic fields generated using, for example, permanent magnets or electro-magnetic sources such as one or more inductive coils or other magnetic transducers.

Figure 2A:
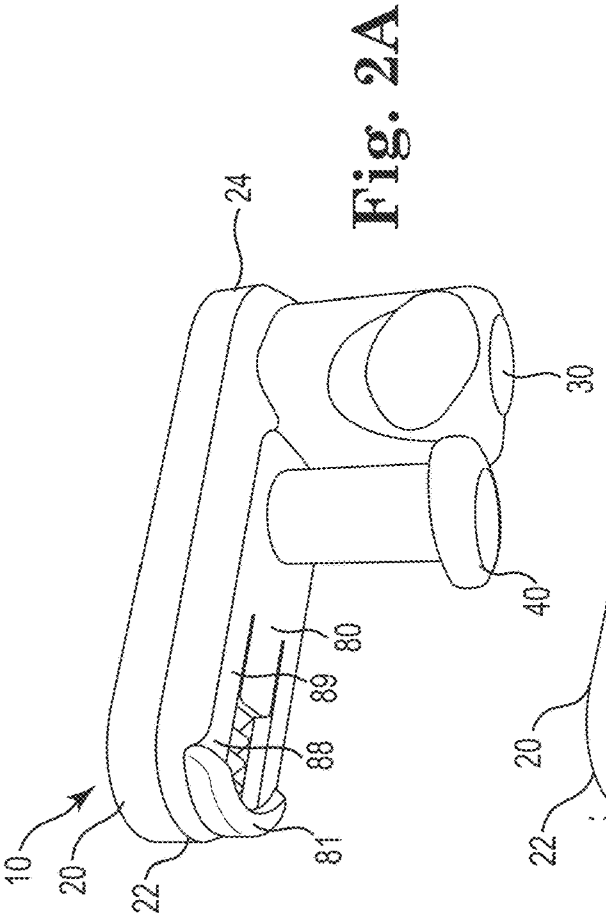
FIGS. 2A-2C are views of a first wearable device.
Figure 2B:
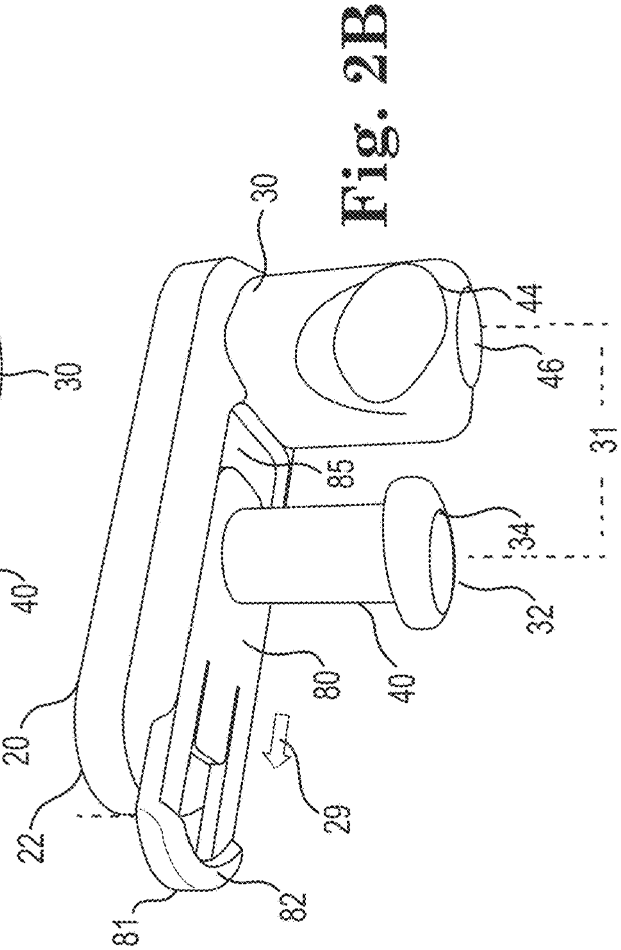
Figure 2C:
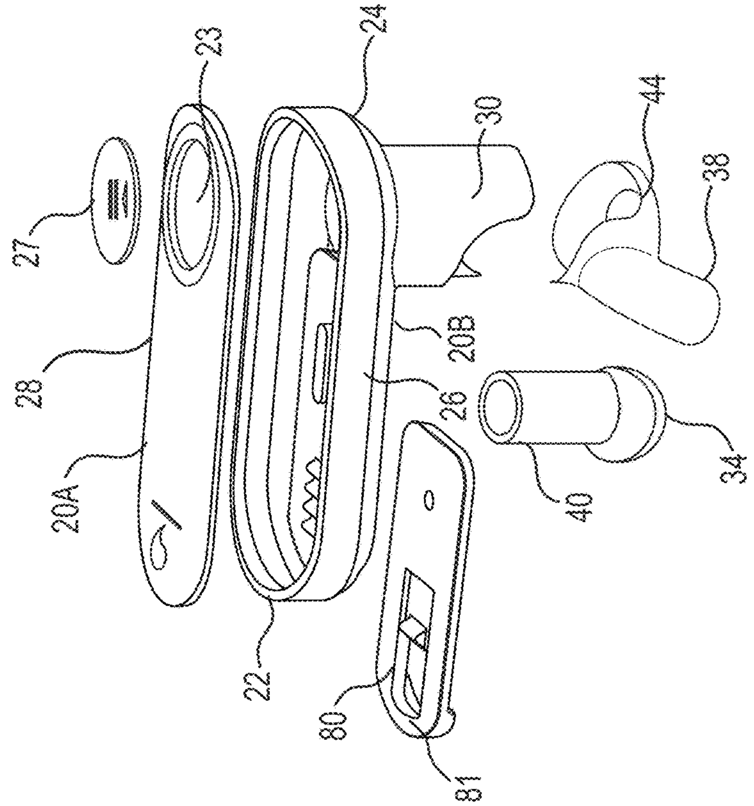

While the example of FIGS. 2A-2C (and similarly FIGS. 3A-3C, 4A-4C, and 5A-5C) is described as having speakers, in some embodiments sensors such as those described herein, other devices, methods and/or modalities can also be used. For instance, some examples herein may be directed to non-therapeutic, sensory, and/or purely auditory devices such as those including a speaker e.g., for the purpose of emitting sound or music to a user of the auditory devices and/or an electrical sensor. However, some examples may include a sensor such as electrical, optical, and magnetic sensors configured to detect or sense galvanic skin impedance, heart rate, heart rate variability, oxygenation, movement or acceleration (e.g., an accelerometer and/or gyroscope), various signals such as nerve and brain signals (e.g., an electroencephalograph), and/or the presence of one or more molecules (e.g., optical or chemical sensors) and/or configured to sense molecules in or on tissue, among other types of sensors. The sensor can be configured to detect or sense one or more of the above mentioned elements, statuses, actions, or characteristics while the devices herein are inserted in an ear of a user. As detailed herein, the sensor wherein a sensor can be positioned on the first extending structure or the second extending structure. In some embodiments, a speaker can be positioned on one of the first extending structure and the second extending structure and the sensor can be positioned on the other of the first extending structure and the second extending structure. However, in some embodiments the speak and a sensor can each be located on either the first extending structure or the second extending structure (e.g., the speaker and sensor are collocated on an individual extending structure).

FIGS. 2A-2C are views of a first wearable device 10. FIGS. 2A-2B are views of the wearable device 10, while FIG. 2C shows an exploded view of the wearable device 10. The device 10 is adapted for placement relative to an ear of a user.

A housing 20 contains electronics and a power source configured for providing output energy, which may come in various forms including, in some examples, electrical pulses or other waveforms. In some embodiments, the electronics comprises an output circuitry to provide power at least to the speaker. Illustrative circuitry is shown and discussed relative to FIG. 10, below.

The housing 20 has a length between a first end 22 and a second end 24, and a width between a first side or edge 26 and a second side or edge 28. The housing can be an elongated housing where the length between a first end 22 and a second end 24 is greater than the width in this example. For example, the length may be in the range of about 10 to about 60 millimeters, and width in the range of about 3 to about 30 millimeters, or more or less. The overall mass of the device 10 may be in the range of about 10 to about 50 grams, or more or less.

The device 10 includes a first extending structure 30 having a first end at the housing 20 and a second end apart from the housing 20. The first end of the first extending structure 30 can by coupled to or proximate to a proximal end of the carriage 80, as illustrated in FIGS. 2A-2B.

The first extending structure 30 has a length, generally in the range of about 3 to about 15 millimeters or more or less. At or near the second end of the first extending structure 30 is an anchor arm 44 extending laterally therefrom. In some examples, the device 10 may be characterized by the anchor arm 44 being configured to be positioned beneath the tragus when the device is placed. In some further examples, the anchor arm 44 is configured to be inserted into the external auditory canal of the user, providing at least a first anchoring point for the device.

Figure 3A:
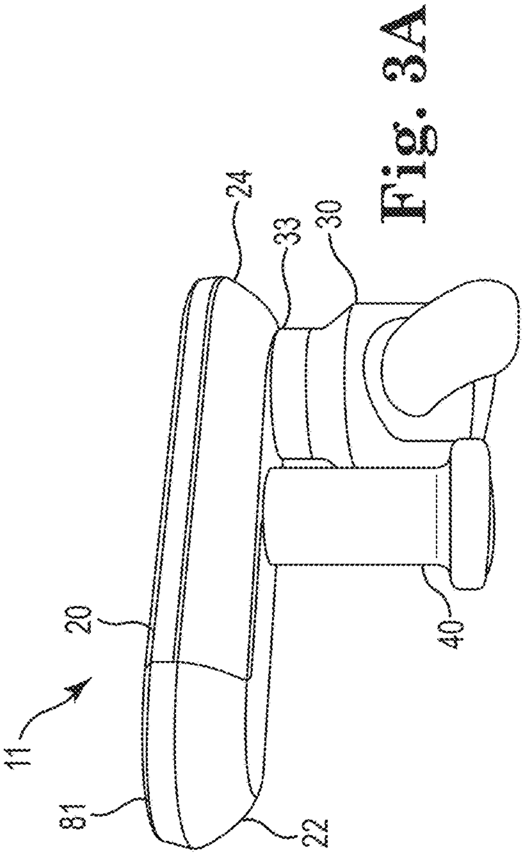
FIGS. 3A-3C are views of a second wearable device.
Figure 5A:
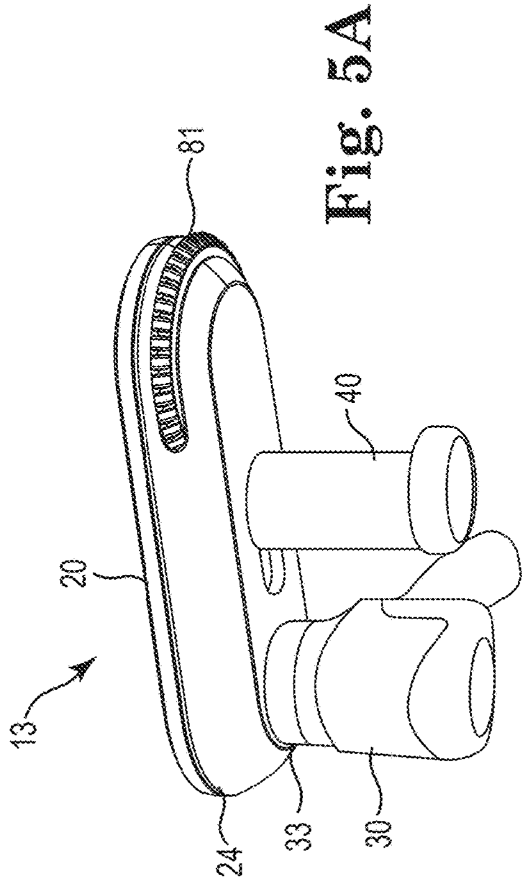
FIGS. 5A-5C are views of a fourth wearable device.

The first extending structure 30 can include a neck portion 33 located along the length of the first extending structure 30. For instance, the neck portion 33 can be located proximate or adjacent to the housing 20, as illustrated in FIGS. 3A and 5A. The neck portion 33 can have a smaller diameter than another portion or the remainder of the first extending structure 30. Stated differently, the neck portion 33 can form an indented portion of the first extending structure 30. In some embodiments, the neck portion 33 can be configured to provide an area into which tissue such as flaps of skin of the tragus and/or antitragus can overlay when the devices herein are inserted into an ear. For instance, the tragus and antitragus protrusions of the ear can desirably apply a force on the first extending structure 30 at the necked portion 33 such that the first extending structure 30 is securely retained in the ear (e.g., in the cavum) and/or an element located on the first extending structure 30 such as a speaker is thereby affixed firmly against the ear (e.g., the cavum). The neck portion 33 can optionally be configured to rotate relative to the housing 20 and/or another portion or the remainder of the first extending structure 30. The degree of rotation of the neck portion 33 can be at least 15 degrees, at least 30 degrees, or at least 45 degrees, among other possibilities.

The housing 20 includes or is attached to a second extending structure 40 having a first end at the housing 20 and a second end apart from the housing 20. The first end of the second extending structure 40 can be coupled to the carriage 80. For instance, the first end of the first extending structure 40 can be coupled to an outer surface such as the lowermost surface of the carriage 80, as illustrated in FIGS. 2A-2B. The second extending structure 40 has a length which may be in the range of about 3 to about 15 millimeters, or more or less. The length of the second extending structure may be variable, for instance, due to the presence of a spring structure or other biasing member or structure to allow flexibility or variability in a length of the housing 20 when the device is placed within an ear of a user.

Figure 3B:
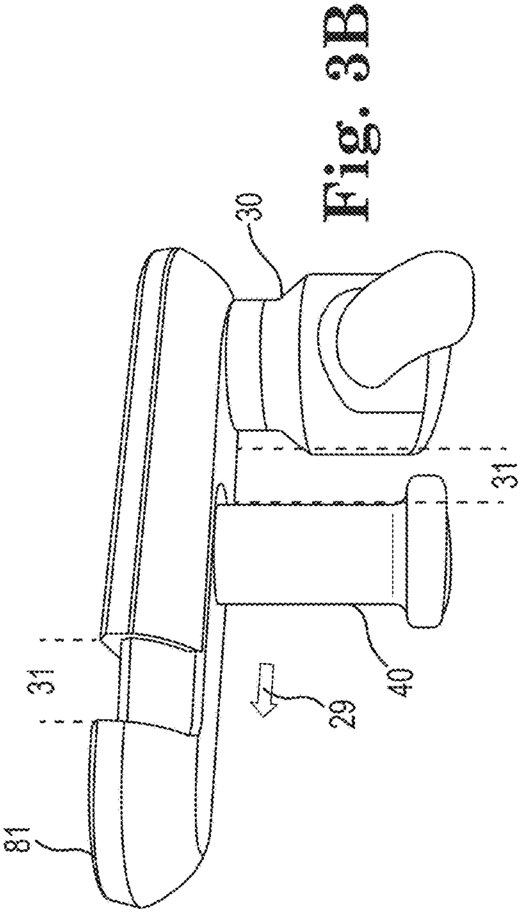

A distance 31 between the first extending structure 30 and the second extending structure 40 can be adjusted. The distance 31 can be taken from a centerline or center point of each of the first extending structure 30 and the second extending structure 40, as illustrated in FIG. 2B or can be taken from opposing surfaces of the first extending structure 30 and the second extending structure 40, as illustrated in FIG. 3B. Hence, the distance 31 can refer to a distance between opposing faces of the respective first extending structure 30 and the second extending structure 40 and/or a distance between a central axis or respective center points of the first extending structure 30 and the second extending structure 40. The distance 31 can extend substantially along a longitudinal axis of the device 10. The distance 31 can be equal to a portion of the length of the device 10. The distance 31 can be adjustable or variable when the device 10 is placed within an ear of a user. For example, the distance 31 may be in the range of about 2 to about 20 millimeters, when the device is inserted in an ear of a user (e.g., when at least a portion of the first extending structure 30 and the second extending structure 40 are inserted in an ear of a user. The distance 31 can be varied by moving (e.g., longitudinally translating) the second extending structure 40 relative to the first extending structure 30. For instance, the first extending structure 30 may be fixed at a given longitudinal position and the second extending structure 40 may be configured to move (e.g., longitudinally translate distally relative to the first extend extending structure 30), as detailed herein. For instance, the second extending structure 40 may be configured to longitudinally translate responsive to actuation of an adjustment mechanism 81. Conversely, the first extending structure may be configured to longitudinally translate responsive to actuation of an adjustment mechanism 81, for example, when the first extending structure 30 is coupled to a proximal end of the carriage 80, and the second extending structure is coupled to the housing. Furthermore, both the first and second extending structures may be configured to longitudinally translate responsive to actuation by one or more adjustment mechanism 81 and carriages 80.

The adjustment mechanism 81, as detailed herein, can refer to an individual adjustment mechanism that is manifested as an individual component. Thus, the adjustment mechanism 81 can be configured to permit readily adjusting the distance 31, even when the device 10 is disposed in a user (e.g., an ear of a user). For instance, the adjustment mechanism 81 can be configured to permit a user (e.g., a user) to adjust the distance 31 while the device 10 is disposed within an ear of the user by actuation of the adjustment mechanism with a single hand (e.g., one or more digits on the single hand), as compared to some other devices which require any adjustment to be performed prior to insertion of a device in the user and/or which require the use of two or more hands to adjust the device. That is, the adjustment mechanism 81 permits precise adjustment of the second extending structure's position relative to the first extending structure's position, ensuring optimal placement of the speaker or audio output device(s) e.g., on the conchae cymba without the need of the user to remove the device from the ear.

The adjustment mechanism 81 can be located at the first end 22 of the housing 20. Having the adjustment mechanism 81 be located at the first end 22 of the housing can promote aspects herein such as permitting a user to readily adjust the distance 31, even when the device 10 is disposed in an ear or a user. For instance, the adjustment mechanism 81 can be located at the first end 22 of the housing 20 and a portion (e.g., first portion) of the adjustment mechanism 81 can be located outside of the housing 20, while another portion of the adjustment mechanism 81 can be located inside of the housing 20. The portion of the adjustment mechanism 81 that extends outside of the housing 20 can thus extend (e.g., in a substantially longitudinal direction) a distance away from the first end 22 of the housing 20. The portion of the adjustment mechanism 81 that extends outside of the housing 20 can be contacted by one or more digits on a hand of a user and the other portion of the adjustment mechanism can be configured to adjust or move the carriage 80 responsive to the contact. The portion (e.g., second portion) of the adjustment mechanism 81 that is inside the housing can be integral with or coupled to the carriage 80. For instance, as detailed herein, the second extending structure 40 can be coupled to the carriage 80. Thus, the movement of the carriage 80 can impart a corresponding movement in the second extending structure 40. For example, actuation of the first portion of the actuation mechanism 81 can directly or indirectly cause the carriage 80 to move, as detailed herein, thereby imparting a corresponding movement in the second extending structure 40 (e.g., in the same direction and magnitude as the movement in the carriage 80).

One or more mechanisms 81 can be integral or coupled to more than one carriage 80 to impart movement on both the first and second extending structures.

Figure 3C:
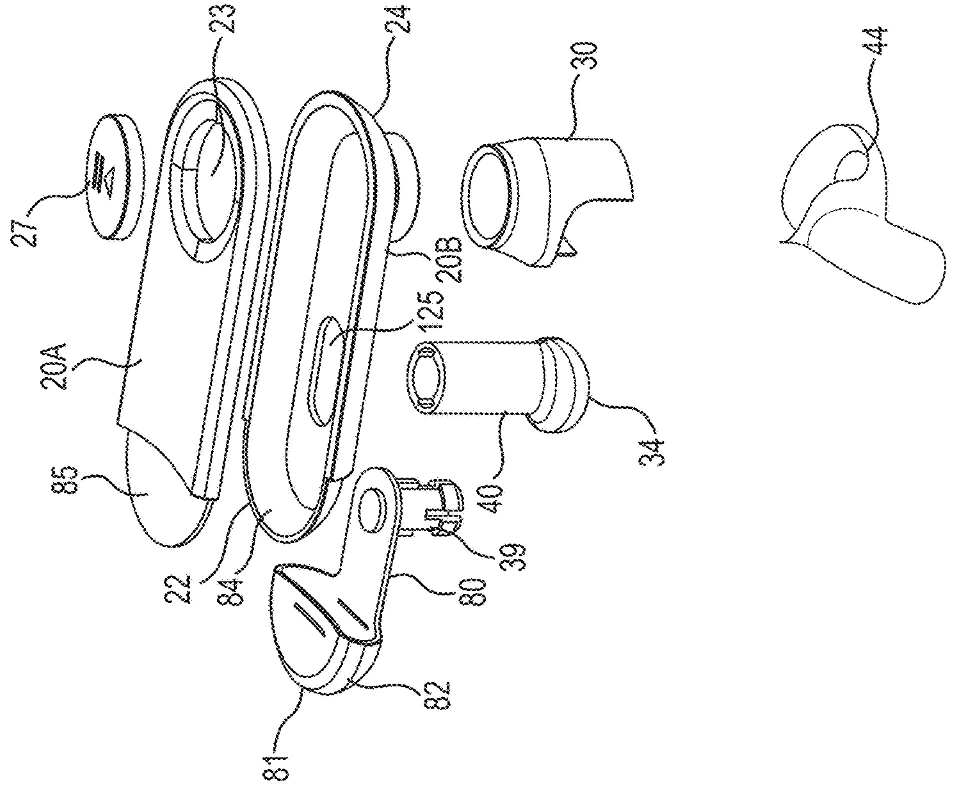

As mentioned, in some embodiments the adjustment mechanism 81 can be integral with the carriage 80. For example, as illustrated in FIGS. 2A-2C and 3A-3C, the adjustment mechanism can be integral with the carriage 80. In such examples, the adjustment mechanism 81 can be located on a first end of the carriage 80. The first end of the carriage 80 refers to an end of the carriage 80 that is spaced away or least proximate to the first and second extending structures. Having the adjustment mechanism 81 be located on or integrally formed in the first end of the carriage 80 can promote aspects herein such as readily permitting a user to adjust the distance 31, even when the device 10 is implanted or disposed in an ear of a user. For instance, the adjustment mechanism 81 can include a fixed protrusion extending radially from the carriage 80. Stated differently, the adjustment mechanism 81 can be formed of an integral fixed protrusion that extends from the carriage 80. For example, the adjustment mechanism 81 can be manifested as a raised surface or protrusion that extends (e.g., radially and/or longitudinally) a distance from the carriage 80, as illustrated in FIGS. 2A-2C. Other configurations of the adjustment mechanism 81 are possible. For instance, the adjustment mechanism 81 can be manifested as a recessed or indented portion of a surface (e.g., an indented portion in an end of a protrusion extending radially from the carriage 80), as illustrated in FIGS. 3A-3C.

As mentioned, in some embodiments the adjustment mechanism 81 can be a separate component that is coupled to the carriage 80. For instance, the adjustment mechanism 81 can be a separate component that is coupled to a first end (e.g., that is spaced away from or least proximate to the first and second extending structures) of the carriage 80. For example, as illustrated in FIGS. 4A-4C and 5A-5C, the adjustment mechanism 81 can be a separate component that is coupled to the first end of the carriage 80. In such instances, the adjustment mechanism 81 can be a rotatable adjustment mechanism such as a rotatable wheel or rotatable lever. For instance, the adjustment mechanism 81 can be a rotatable adjustment mechanism including an annulus (e.g., annulus 93, as illustrated in FIGS. 4C and 5C), wherein the rotatable adjustment mechanism is configured to rotate about the annulus 93 relative to the carriage 80, the housing 20, or both the carriage 80 and the housing 20, as detailed herein. Hence, the rotatable adjustment mechanism (e.g., a rotatable lever or rotatable wheel) can be configured to rotate about a plane (extending through the annulus 93) that is normal to a longitudinal axis of the device 10 such that rotation of the adjustment mechanism imparts a force to cause longitudinal movement (e.g., translation) of the carriage 80, as detailed herein.

In some embodiments, the carriage 80, the actuation mechanism 81, and/or the housing 20 can include detents that are configured to predispose the carriage 80 to corresponding longitudinal positions along a length of travel (e.g., longitudinal translation) of the carriage 80. Employing detents can promote aspects herein such as promoting retention of the devices herein within an ear of a user i.e., once the carriage 80 is disposed at a given longitudinal position corresponding to one or more of the detents. For instance, the presence of the detents can permit the carriage 80 to move between and be disposed in one or more fixed positions (e.g., three different longitudinal positions) to accommodate different sized ears (e.g., small, medium, and large sized ears) of various users of the devices herein.

The detents can be mechanical detents and/or magnetic detents (e.g., formed of two or more magnets including a magnet coupled to the carriage 80 and a magnet coupled to the housing 20). For instance, the carriage 80 can include detents located along one or more of the substantially longitudinally extending side surfaces of the carriage 80 and/or that are located along the elongated slot 98 or other aperture in the carriage 80. In some embodiments, the detents of the carriage 80 can be manifested as one or more substantially radially projecting arms or features. In some embodiments, the detents of the carriage 80 can be manifested as a series of undulating ridges (e.g., peaks and valleys disposed therebetween). The detents can be configured to predispose the carriage 80 to longitudinal positions associated with the valleys (e.g., at spaced intervals between adjacent valleys), while the peaks can be configured to provide a degree of resistance to the longitudinal movement (e.g., translation) of the carriage 80. The housing 20 can include one or more corresponding detents or projections that are configured to mechanically interfaces with the detents of the carriage 80. In some embodiments, the corresponding detents 89 can be manifested as one or more arms or projections or as a series of undulating ridges (e.g., peaks and valleys). In some embodiments, the corresponding detents 89 can be manifested as one or more pegs or projections, as illustrated in FIG. 4C.

As detailed herein, the carriage 80, the housing 20, or both the carriage 80 and the housing 20 can include detents that are configured to predispose the carriage to one or more longitudinal positions along a length of travel of the carriage 80. For example, FIG. 4C illustrates the presence of detents 88 along a substantially longitudinally extending surface of the elongated slot 98. In such instances, the housing 20 can have a corresponding substantially longitudinally extending surface with corresponding detents. For example, an interior surface (most proximal to the carriage 80) of an elongated peg 99 can include detents 89 that are configured to interface with (e.g., interference fit with) the detents 88 and permit the carriage 80 to be moved longitudinally between one or more positions at which the detents 88 of the carriage 80 and the corresponding detents 89 of the housing 20 predispose the carriage 80.

In some embodiments, the location of the detents 88 of the carriage 80 and/or the location of the corresponding detents of the housing 20 can be varied for the locations in FIG. 4C. For instance, the detents 89 of the housing 20 can be located on one or both of the molded pieces 20A, 20B. In other examples, the detents can be located on the adjustment mechanism 81, the housing 20, or both the adjustment mechanism 81 and the housing 20. For example, detents 88 can be located on the adjustment mechanism 81 along at least a portion of an exterior surface of the adjustment mechanism 81 and the housing 20 can include corresponding detents 89 that are configured to interface with the detents 88 on the actuation mechanism 81. An example of alternative locations for the detents 88 and the corresponding detents 89, is indicated in FIG. 2A.

Alternatively, or in addition to varying the location of the detents 88 and/or the corresponding detents 89, the structures of the detents 88 and/or the corresponding detents 89 can be varied.

For instance, one of the detents 88 and the corresponding detents 89 can be manifested as a peg or projection, while the other of the detents 88 and the corresponding detents 89 can be manifested as a series of undulating ridges (e.g., peaks and valleys). For example, the detents 88 can be configured as a series of undulating ridges and the corresponding detents 89 can be manifested as one or more peg or projection that is configured to interface with the detents 88, as illustrated in FIG. 4C, or the detents 88 can be configured as a peg or projection and the corresponding detents 89 can be manifested as a series of ridges (e.g., peaks and valleys).

The housing 20 may comprise molded pieces 20A, 20B assembled together. In this example, the first molded piece 20A may be an upper lid and a second molded piece 20B may have a lower container to which the upper lid attaches, collectively forming housing 20. In this example, the first extending structure 30 is shown to be integrally molded or otherwise formed as an integral part of the lower container 20B or another portion of the housing 20. In other embodiments, the second extending structure 40 can be integrally molded or otherwise formed as an integral part of with the lower container 20B or another portion of the housing 20. Molded into the lower container 20B is an internal channel 85 configured to receive carriage 80. However, other configurations of the lower container 20B and the carriage 80 such as those having the internal channel 85 in a different location or an absence of the internal channel 85 are possible. In some examples, the carriage 80 and the upper portion (most proximate to the carriage) of the second extending structure 40 may be molded together as a singular piece for positioning into the internal channel 85.

In some embodiments, the lower container 20B also includes an elongated aperture 125, situated between the first extending structure 30 and the first end 22 of the housing 20, for instance, as illustrated in FIGS. 3C, 4C, and 5C herein. In such embodiments, the carriage 80 can include a lower portion the extends through the aperture 125 to contact an upper portion of the second extending structure 40. Alternatively, an upper portion of second extending structure 40 can protrude through the aperture 125 away from the housing 20. In any case, the position of the carriage 80 in housing 20 (e.g., the position of the carriage 80 within the internal channel 85) is adjustable, and by virtue of the second extending structure 40 being coupled to carriage 80, the position of the second extending structure 30 is also adjustable. That is, the space between the first extending structure and the second extending structure is adjustable.

In some embodiments, the aperture 125 allows the second extending structure 40 to protrude through the lower container 20B and the internal channel 85 exceeds the length of the aperture 125, providing a guided pathway for the carriage 80 to slide within the lower container 20B.

As a consequence of such configuration, the range of the carriage 80 movement can be limited to the extent that the second extending structure 40 can moveably slide within the bounds of the elongated aperture 125. This range of movement is illustrated, for instance, in part by the arrow 29 in FIG. 3B. By limiting such movement to the range allowed by the elongated aperture 125, manufacturing and assembly are made easier than if the housing had two components which slide together and apart, as controlling the maximum extent of movement is relatively simple. In an alternative example, rather than an aperture as shown in FIG. 3B, the overall housing 20 may have first and second components that mate together in sliding fashion to allow the length of the housing itself to be varied.

In some examples, a shroud or cover can overlay a portion of or an entirety of the apertures described herein. The shroud or cover can be configured to prevent or mitigate ingress of material (e.g., liquids and/or particulate materials). The cover can be formed of a relatively thin and/or deformable sheet of material. Examples of suitable materials for the cover include various thermoplastics (e.g., polyethylene, polypropylene, polyvinyl chloride, Polyethylene Terephthalate, EVA (Ethylene Vinyl Acetate), Polyamide (Nylon), among others. In some examples, the cover can be located internal to the housing 20 and permit a component such as at least a portion of the carriage 80 to project through the cover to a location outside of the housing 80, for instance, to mitigate ingress of material into the housing 20.

During or subsequent to placement of the device in the ear of the user, a position (longitudinal position) of the carriage 80 can be adjusted such that the sensor 32 is positioned on a conchae cymba while the first electrode or speaker 46 is positioned desirably at the conchae caverna. Yet, in some examples, the second electrode or sensor 32 may be positioned at the conchae caverna. In this configuration, the second electrode or sensor 32 is not part of the second extending structure 40, but rather integrated into housing 20 or the first extending structure 30, enabling the second electrode or sensor 32 to be in contact with different areas of the conchae once the device 10 is in position. In this example, the second extending structure 40 remains useful for stabilizing and securely attaching the wearable device 10 to the ear, regardless of whether a sensor or speaker is carried thereon.

In some examples, the user may adjust the positioning of the second electrode or sensor 32 by manipulating a position of the carriage 80 with the housing 20 from outside of the device e.g., wearable device 10. By enabling adjustment from outside of the wearable device 10, the wearable device 10 does not have to be removed from its previously secured location (e.g., within an ear). This form of manipulation also enables precise adaptation to individual ear anatomies, without compromising the stability of the wearable device 10 placement as previously positioned. Adjustment of the carriage 80 in the housing 20 (e.g., within the internal channel 85 in the housing 20) may be done manually or via a spring-loaded mechanism. In the examples that use a spring-loaded mechanism, the mechanism can be compressed during wearable device 10 placement in the ear and subsequently released to expand relative to a portion of the ear (e.g., the inferior crus, helix, or antihelix), effectively securing the wearable device 10 in the ear. This expansion creates a counterforce against the conchae cavum, so that the first extending structure 30 is in contact against tragus and/or anti-tragus, ensuring a snug fit. In some examples, the spring-loaded mechanism incorporates a latch system, allowing the wearable device 10 to be locked in various positions between fully compressed and fully extended states. This allows further customization the fit and positioning of the wearable device 10 in accordance to the user's ear anatomy and comfort preferences, while maintaining the device's stability and effectiveness. In the manual configuration, users may adjust the positioning as needed including, but not limited to, using their fingers, tabs, hooks, loops, or pivoting levers. This adjustment can be done either before or after wearable device 10 has been placed in the ear.

The second extending structure 40 may have a variable shape, allowing for bending to a desired angle, and/or may rotate or pivot, so that the device can be adjusted to fit the user's ear. For example, FIG. 10D illustrates a variable length and pivoting mechanical structure; in other examples the structure itself may be flexible.

As mentioned, in some examples, the housing 20 comprises molded pieces assembled together. For example, a first molded piece 20A may be an upper lid and a second molded 20B piece may be a lower container to which the upper lid attaches, thereby substantially forming the housing 20. Other manufacturing methods can be used. The first extending structure 30 may be a molded part of a lower container forming part of the housing 20, with the anchor arm 44 or a portion thereof included as part of the molding step, or attached thereto in a subsequent manufacturing step. Other assembly or manufacturing methods can be used. The example shown here includes a first electrode or a speaker 46 on the first extending structure 30, and, optionally, a second electrode or sensor 32 on the second extending structure 40. There may be more than one electrode or element in each of these locations. Some examples may omit the second electrode or sensor 32 and/or may omit the first electrode or speaker 46. Rather than electrodes at 32, 46, devices for creating other therapy outputs (transducers, for example, for optical, mechanical/vibratory, magnetic, thermal or other therapies) may be used, in which case at least one transducer may be positioned on the first extending structure 30 and/or the second extending structure 40. Desirably, the positioning and/or degree of insertion of the anchor arm 34 may be such that the second electrode or sensor 32 and the first electrode or speaker 46 come into contact with the skin in the ear of the user.

The anchor arm, or "wing" 34, located at the second end of the second extending structure 40 may have an expanded end portion coupled by a thinner portion coupled to the second extending structure. Stated another way, the radial dimensions of the anchor arm or wing 34 may extend outward beyond (e.g., be larger than) the radial dimensions of the extending structure 40, as shown for example by FIG. 2B. The radial dimensions of the anchor arm or wing 34 may vary around its perimeter to form one or more edges or "lips" of varying size. The one or more ridges or lips of the anchor arm or wing 34 may be placed under the ridges and folds of skin formed by the helix, inferior crus, and antihelix. In some examples, when an illustrative device (e.g., the device 10) is placed in the ear, a portion of the anchor arm or wing 34 proximal to the helix may extend further than a portion of the anchor arm or wing 34 proximal to the inferior crus and antihelix, as appropriate to fit within the depths of skin folds formed by the helix, inferior crus, and antihelix. The curvature of the perimeter of the anchor arm or wing 34 may vary to optimally fit the curvature of the outer boundaries of the cymba formed by the helix, inferior crus, and antihelix. In some examples, the anchor arm or wing 34 may be rigidly coupled to the second extending structure 40. In some examples, the anchor arm or wing 34 may rotate relative to the housing 20. Rotation of the anchor arm or wing 34 may permit an improved fit to varying curvatures or differing geometries of the helix, inferior crus, and antihelix across users of the devices herein. The device 10 can be configured such that a distance between the first extending structure 30 and the second extending structure 40 is adjustable. For instance, adjustment of the distance between the between the first extending structure 30 and the second extending structure 40 can be adjustable via actuation or movement of the carriage 80. In such instances, movement of the carriage 80 can impart a corresponding movement (e.g., of the same magnitude and direction) in the second extending structure 40 and anchor arm or "wing" 34 e.g., as the anchor arm 34 is coupled to the first extending structure 40, which is coupled to the carriage 80. The device 10 can be configured such that the anchor arm or "wing", 34, is positioned under any portion of the helix, inferior crus, and antihelix such that any portion of a ridge, or lip, of the anchor arm or wing 34 is held against the ear and resists dislodgement of the device 10 when a counter force is imparted against the tragus and antitragus when the carriage 80 is extended.

As highlighted in FIG. 2C, the anchor arm 44 may include an expanded or bulbous end portion coupled by a thinner portion to the first extending structure 30. While a bulbous end portion is shown, other shapes (oval, polygon, tapered, conical, etc.) may be used instead, and/or the end portion can be or include a foam material that can be compressed prior to placement, and then expands to secure the device in an anchored position. Alternatively, in other examples, the anchor arm 44 may have a consistent or tapered outer profile from its connection to the first extending structure 30 to its tip. The anchor arm 44 and end structure 38 may be a unitary or single piece, and may be hollow to allow audio signals to pass therethrough. In some examples, a speaker may be integrated into the device to deliver audio signals. The anchor arms herein such as the anchor arm 44 may also include one or more electrodes, sensors, and/or a speaker thereon. The anchor arm 44 and/or end structure 38 may be provided as a detachable/replaceable piece that can be selected from a range of sizes or shapes. In some examples, the anchor arm 44 and/or end structure 38 thereof may be formed of a compliant material to conform to the space under the tragus and/or inside the auditory canal.

The anchor arm 44 may extend at an angle relative direction of the length of the housing. The angle can be about ninety degrees, but in other examples it is envisioned that the angle can be in the range of about 60 to about 120 degrees, or about 70 to about 110 degrees, or about 80 to about 100 degrees. In an example, the angle of the anchor arm 44 may be adjustable, if desired, such as by use of a click-mechanism or flexible material to allow the anchor arm 44 to twist about the first extending structure 30. In still another example, the first extending structure 30 may be adjustable to twist about, for example, a central core (e.g., necked portion 33), entirely or through a limited range of motion such as (using the angle of the anchor arm as a guide) between about 60 to about 120 degrees, or more or less as desired. In the illustrative example shown in FIGS. 2A-2C, 3A-3C, 4A-4C, and 5A-5C, the position of the anchor arm 44 is fixed. One or more stops may be included to limit the translation, extension or rotation of the anchor arm 44, to the extent it is adjustable. The first and second extending structures 30, 40 may likewise be adjustable in terms of translation, extension/retraction and/or rotation, as desired.

If desired, one or more through-openings or holes may be provided in the anchor arm 44 to allow air ingress/egress, facilitating hearing for the user by avoiding complete blockage of the auditory canal. The anchor arm 44 may further include one or more electrodes, sensors and/or transducers, either for therapy purposes or to enable or augment hearing of a user or to emit music. For example, a speaker may be provided, allowing the user/user to hear audible indications of device and/or therapy status, to amplify sounds (as with a hearing aid), or to provide entertainment or communications to the user/user.

In first example, when the device 10 is placed relative to the ear of the user, the anchor arm 44 is positioned to extend beneath the tragus, while the second electrode or sensor 32 is positioned at (i.e. in contact with) the conchae cymba, and the first electrode or speaker 46 is positioned at (i.e., in contact with) the conchae caverna. In second example, when the device 10 is placed relative to the ear of the user, the anchor arm 44 is positioned to extend beneath the tragus, while the second electrode or sensor 32 and the first electrode or speaker 46 are on opposing sides of the crus helix. In a third example, when the device 10 is placed relative to the ear of the user, the anchor arm 44 is positioned to extend into the auditory canal, while the second electrode or sensor 32 is positioned at (i.e., in contact with) the conchae cymba, and the first electrode or speaker 46 is positioned at (i.e. in contact with) the conchae caverna. In an example, when the device 10 is placed relative to the ear of the user, the anchor arm 44 is positioned to extend into the auditory canal, while the second electrode or sensor 32 and the first electrode speaker 46 are on opposing sides of the crus helix. For instance, In an example, when the device 10 is placed relative to the ear of the patient, the anchor arm 44 is positioned to extend into the auditory canal, while the first and second electrodes are on opposing sides of the crus helix. These examples are not intended to be an exhaustive list of descriptions of the device positioning.

The electrodes herein may each have a surface area in the range of about 20 $mm^2$ to about 100 $mm^2$, or more or less. In some examples, each electrode as an area in the range of about 25 $mm^2$ to about 80 $mm^2$. The first electrode (e.g., element 46) may be larger than the second electrode (e.g., element 32) in some examples, allowing stimulation to be more targeted to the region of the second electrode by increasing the current density in the vicinity of the second electrode. The space or gap (edge to edge) between the electrodes may be in the range of about 2 mm to about 15 mm, or more or less. For example, electrodes may be about 5 mm to about 10 mm apart (edge to edge). Voltage and/or current controlled output waveforms may be used, as further described below. In some embodiments, the electrodes herein (e.g., the electrodes 32, 46) may be textured for instance to etching, scoring, pitted, porous, or comprised of one or more partially compressed strands. Employing textured electrodes (with a textured surface) can increase the surface area of the electrodes, thereby, decreasing interfacial impedance with the skin or interference through an applied conductive gel.

In some embodiments, the device 10 can be affixed to the ear in an absence of a clip, tape, and/or another type of attachment mechanism. For instance, as illustrated in FIGS. 2A-2C, the device 10 does not include a clip or adhesive tape. Instead, the device can be secured in place by the extending structures themselves and the anchor arms 44 and 34. The second extending structure 40, in some embodiments, aids in holding the device by having a variable length, using, for example, a spring loaded or otherwise adjustable connection between the upper part and lower part thereof, holding the second electrode or sensor 32 on the skin of the user while the anchor arm (or "wing") 34 of the second extending structure 40 holds the device in a desired position and secures the placement of the second electrode or sensor 32. For instance, abutment of the second extending structure to a first portion of an ear (e.g., the inferior crus and antihelix) creates an opposing force to the first extending structure positioned against a second portion of the ear (e.g., the antitragus). Stated differently, in some embodiments the second extending structure is configured to abut a first portion of an ear to create an opposing force to the first extending structure which is configured to abut a second portion of the ear, wherein the first portion of the ear is the inferior crus, the antihelix, or both, and wherein the second portion of the ear is the antitragus. As detailed herein, the speaker, electrode, and/or a sensor can be located on the first extending structure and/or the second extending structure. Hence, the speaker, electrode, vibrating element, and/or sensor located on one or both of the first and second extending structures can readily function in various manners such as to convey sound to the ear of the user, deliver stimulation (e.g., electrical stimulation), and/or sense one or more parameters of conditions of the ear e.g., while the second extending structure abuts the first portion of the ear to create the opposing force to the first extending structure which abuts a second portion of the ear. Additionally, in some embodiment abutment of the anchor arm or wing of the second extending structure in the ear (e.g., beneath the anterior fold of the helix superior to the tragus) creates an opposing force to posterior rotation of the device relative to the ear, as does abutment of a portion of the anchor arm or wing of the second extending structure in the ear (e.g., beneath the fold of the inferior crus and/or antihelix). Optionally, the examples herein can also include a clip (not illustrated), adhesive tape, or other for clipping the device 10 into a desired position in the ear of a user.

Thermal stimulation may include heating of the nerve; heating may be achieved either by issuing higher frequency signals (RF heating), or by the use of a resistive heating element, for example and without limitation, wherein the resistive heating element may serve as a thermal transducer. Cooling may be provided, such as by having a removeable/replaceable thermal element that can be placed in a refrigerator prior to use, by including a Peltier cooling apparatus, or by having channels allowing cooling fluid to be circulated, either of which may be a thermal transducer. Thus, rather than the electrodes described above, one or more transducers can be used to convert stored power (usually electrical power from a battery) to a different energy modality. Each of these methods offers unique advantages and may be tailored to specific applications based on factors such as precision, invasiveness, and compatibility with the nerve tissue. For example, optical stimulation offers precise control over the timing and location of nerve activation. Acoustic and magnetic stimulation techniques can penetrate deeper tissues and may be non-invasive, making them suitable for certain clinical scenarios. Thermal stimulation, on the other hand, can modulate nerve activity by altering temperature gradients within the tissue.

In some examples, a combination of modalities can be used. For example, thermal stimulation may be generated by the use of higher frequency (RF) outputs from electrodes, paired with lower frequency pulsed electrical field outputs at frequencies in the tens to hundreds of hertz. Such signal combinations may be delivered in an overlapping or simultaneous manner, or the device may cycle between one therapy mode and another, as desired. Electrical stimulation can also be paired with magnetic, acoustic/vibratory (oscillating), and/or optical stimulation. Other combinations can be used as well.

Separate therapy may also be provided, such as with the delivery of anti-inflammatory or other medications to the patient along with the issuance of stimulation signals, or by also providing circulatory or respiratory support to the patient and/or additional stimulation signals, or thermal controls such as inducing therapeutic hypothermia or other temperature management. In some examples, therapy combined with an analgesic to ensure that the patient will not feel the therapy delivered by the stimulation device. An analgesic may be systemically delivered (injection, oral, etc.) or may be locally delivered such as by elution from the electrode surfaces or by using a gel or liquid containing analgesic substances (such as lidocaine) on the electrode surfaces.

The device may coordinate therapy delivery with other actions. In some examples, the device may be commanded to start a therapy session, while another therapeutic activity is ongoing, such as having the patient engage in a memory game or other activity while therapy is being delivered. Coordinated timing can be facilitated by use of the controls on the device itself, or the device may include communications circuitry (such as a BLUETOOTH® or BLUETOOTH® Low Energy antenna and chip) to communicate with a programming device or smartphone having counterpart communications circuitry; an application operating on the programming device or smartphone can be used to start therapy at a desired time and/or otherwise operate the devices herein (e.g., to cause a speaker in the device to emit sounds or music). Other coordination may include the use of biological signals. Heart rate, for example, can be monitored by the device itself (such as by adding or including an earlobe clip), or by a second device such as a cardiac monitor; when the heart rate is above a threshold, such as a threshold in the range of 100 to 140 beats per minute (or other setting), the patient may be experiencing a high degree of inflammatory response, so therapy can be turned on in response to elevated heart rate. On the other hand, if the heart rate becomes bradycardic, such as below about 40 to 60 beats per minute, therapy may be stopped. In another example, pupillometry can be used to turn therapy on or off by obtaining an image of the eye, using a smartphone or other device having a camera, and modulating or turning therapy on or off in response to the results of such measurements. Synchronization to other therapies, including physical therapy, drug delivery, or any other intervention can be useful to augment the patient's response to other therapies by Vagus nerve stimulation.

Portion of the housing and/or the speaker and/or sensor elements of the device can be designed to be modular, allowing for easy customization and adaptability to individual user needs. This feature enables users to easily change out the speaker and/or sensor as necessary, providing a tailored device for each user. For instance, the modular design enhances the versatility and flexibility of the device, ensuring that it can be easily adjusted to accommodate different anatomic requirements. Modularity may be provided by, for example, providing aspects of the device housing and/or neural stimulation elements in the system in a range of sizes or types. For example, if electrodes are used to issue electrical stimuli, the electrodes may come in different sizes (surface areas) and/or shapes, which may be selected and/or replaced. Modularity may be provided by, for example, providing aspects of the device housing and/or speaker, electrode, or sensor elements in the system in a range of sizes or types. For example, if a speaker is used to emit sound waves, the speaker or a portion of the housing on or in which the speaker resides (e.g., an earbud) may come in different sizes (surface areas) and/or shapes, which may be selected and/or replaced. Aspects of the housing and the extending structures can also be adjustable or replaceable to accommodate different anatomies (larger or smaller ears), including, for example, pediatric sized systems for smaller ears. The system itself may come in a range of sizes, if desired.

The device may be controllable and/or programmable or reprogrammable, such as by plug-in-type attachment to a port located on the device, or by use of magnetic/inductive, wireless (RF, such as BLUETOOTH®) communication, optical communication, or by having one or more buttons, dials, or other user-accessible controls accessible on the device. To this end, as discussed further below with reference to FIG. 10, a communications circuitry may be included in the device.

The materials used throughout may include any material suitable for skin contact for an extended period of time (hours, days or even weeks).). For an electrical stimulation system, the electrodes, for example, may be made of any of graphene, titanium, nickel titanium (nitinol), platinum, platinum-iridium, gold, silver, stainless steel (including MP35N alloy) or any other metal or conductive polymer or other material that can be worn on the skin. Coating layer(s) may be provided to optimize tissue interface characteristics, as desired.

The electrodes herein may be configured to receive or carry thereon a conductive material, such as a gel, hydrogel, or other tissue interface component. Pads may be attached if desired. Alternatively, dry electrodes can be used, if desired. The other tissue contacting portions of the devices herein may be made of suitable plastics, silicone, etc. adapted for wear on the skin of a patient/user.

Biocompatible materials may be selected to enhance conduction of the therapy signal between the electrode or therapy generating element and the tissue (electrical conduction, mechanical conduction, optical transmission, etc.). Biocompatible materials may also be selected to enhance adhesion of the therapy generating element and the tissue. Biocompatible materials may also be selected to provide an analgesic effect to suppress perception of the therapy. All types of materials may also be combined into a single material. Materials may be attachably and detachably connected to the therapy-generating element. For example, hydrogel pads may be replaced. In cases of wet materials, one or more moisture barriers (e.g. metal foil) may be used for packaging and temporarily adhered over the material to preserve functionality for extended shelf life. In other examples, materials may be separately packaged within a preserving pouch, packet, or container and applied prior to use. In some cases, the material may include a barrier material or membrane that is removed prior to use. In some cases, the barrier material or membrane may include extensions, tabs, buttons, or other structures to aid in handling the material while attaching the material or removing the material from the device.

For instance, in some cases the conduction-enhancing materials or conduction-enhancing pads may be removably coupled or non-removably coupled to the ear-worn devices herein. Examples of removable coupling mechanism include a snap, button, pin, hook and loop coupling systems, and magnets, among other possibilities. In some cases where an attachable conduction-enhancing material or pad is used, an electrode that is integrated with the ear-worn devices herein can take the form of an electrical connector of various geometry including geometry that is configured to at least in part directly contact skin and/or with geometry that is configured to indirectly provide electrical stimulation, via conduction-enhancing material or pad, to skin of a user. Examples of suitable electrode geometries include a disc geometry and a dome geometry, among other possible shapes. The housing 20 optionally includes indicator lights such as status indicator lights and/or alert lights. If desired, an electrode, vibrating element, sensor, and/or speaker may be included in or on the housing 20 as well and used for issuing audible alerts, instructions for use, device status, or other purposes such as for providing an audible signal for entertainment or relaxation purposes (playing music for example). The status indicator lights may be light emitting diodes (LEDs) or any other suitable light generator, as desired.

In some embodiments, the device 10 can include one optical indicator for providing an indication of a state of the wearable device. For instance, the at least one optical indicator can be manifested as a multi-purpose light-emitting diode configured in a ring 351, as detailed herein.

The devices herein such as can contain a transceiver, such as a BLUETOOTH® chip and antenna, to permit communication with an external device such as a smartphone or tablet. Alternatively, or in addition, in some embodiments the devices herein can include a port configured to receive a cable or a cord that can communicatively couple the devices herein to another device (e.g., a smartphone) that is configured to operate the devices herein. Other communication means can be used, including optical, magnetic/inductive, vibratory, etc., as desired. Alternatively, one or more buttons on the device may be used to increase or decrease output amplitude, as desired; additional indicators on the device may be used to allow amplitude settings to be determined visually. Some systems may, on the other hand, be pre-programmed with limited or no therapy adjustments available.

Some of the preceding examples indicate the use or possibility of reshapeable first extending structure 30 and/or second extending structure 40, or an anchor arm 44, or an anchor arm 34, which are reshapeable. Other examples make each of these pieces a rigid element not allowing for reshaping. In some examples, a rigid second extending structure 40 has a spring or other resilient member therein allowing the length to vary in response to user anatomy. The device may then be placed by inserting the anchor arm 44 with its end in the auditory canal of the user, and then twisting the device to bring the second extending structure into contact with the conchae cymba. The twisting movement may be as indicated by arrow and line 260 in FIG. 6, below, until the second extending structure 40 or attached anchor arm (or "wing") 34 abuts the crus helix or antihelix, as explained relative to FIG. 6.

FIGS. 3A-3C are views of a second wearable device 11. The second wearable device 11 is analogous to the first wearable device 10 with the change that the adjustment mechanism 81 and components associated therewith (e.g., in contact therewith) are different. For instance, as illustrated in FIGS. 3A-3C, the adjustment mechanism 81 can include a protrusion 82 extending radially from the carriage 80 in a second direction (toward the first molded piece 20A), whereas the adjustment mechanism 81 of the first wearable device 10 is a protrusion 82 extending radially from the carriage in a first direct (away from the first molded piece 20A). Moreover, the adjustment mechanism 81 of the carriage 80 can be the first end 22 of the second wearable device 11, whereas the first end 22 of device 10 can be formed of the housing 20 (e.g., the carriage can move distal to the first end 22 of the device 10). Additionally, the protrusion forming the adjustment mechanism 81 of the second wearable device 11 can have an indented or recessed portion configured to be contacted by a user, whereas the protrusion forming the adjustment mechanism 81 of the first wearable device 10 can be a tab with planar surface that is configured to be contacted by the user.

Further, the carriage 80 of the second wearable device 11 can include an extended portion 39 configured to extend through an elongated aperture 125 formed in the second molded piece 20B of the housing 20. The extended portion 39 can be configured to be inserted in and coupled to the second extending structure 40 e.g., via a friction fit or interference fit of tabs or ribs located on an end or other portion of the extended portion 39 within an opening in the second extending structure 40. In contrast, second molded piece 20B of the housing 20 of the first wearable device 10 does not include an elongated aperture 125. Instead and as mentioned, the carriage 80 of the first wearable device 10 can be located within the channel 85 formed in an exterior bottom surface of in the second molded piece 20B of the housing 20 and the second extending structure 40 can be coupled directly to a substantially planar surface of the carriage 80, as illustrated in FIGS. 2A-2C.

Figure 4A:
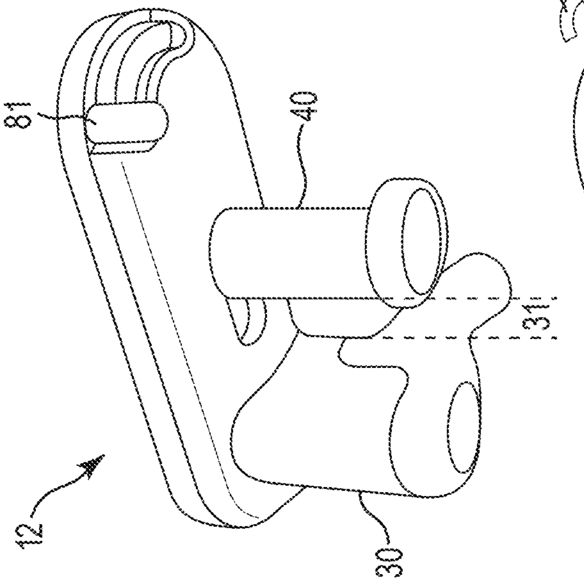
FIGS. 4A-4C are views of a third wearable device.
Figure 4B:
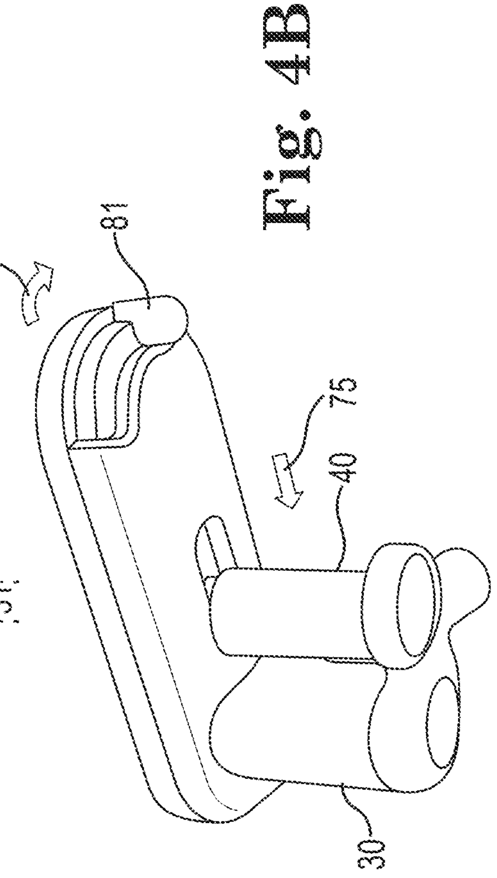
Figure 4C:
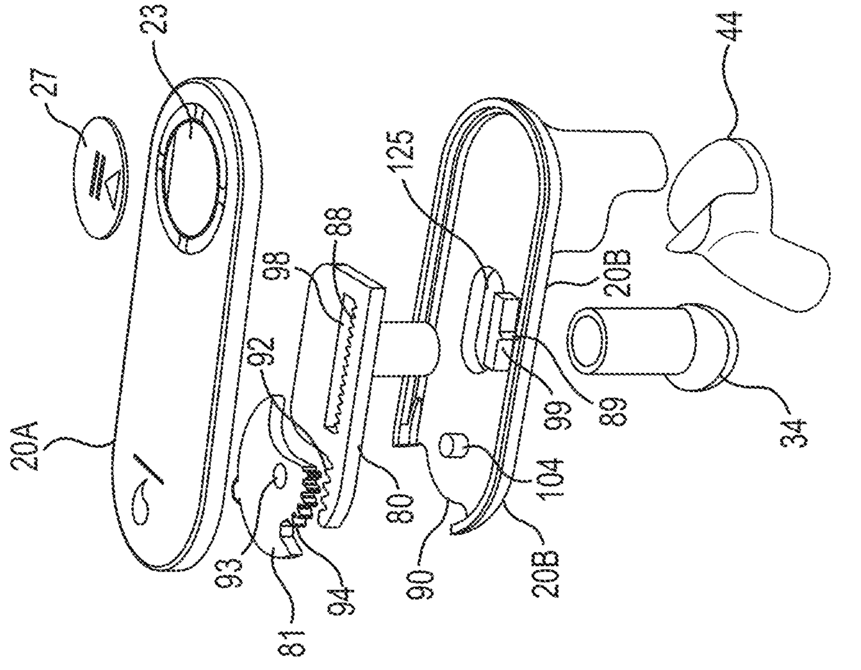
Figure 5B:
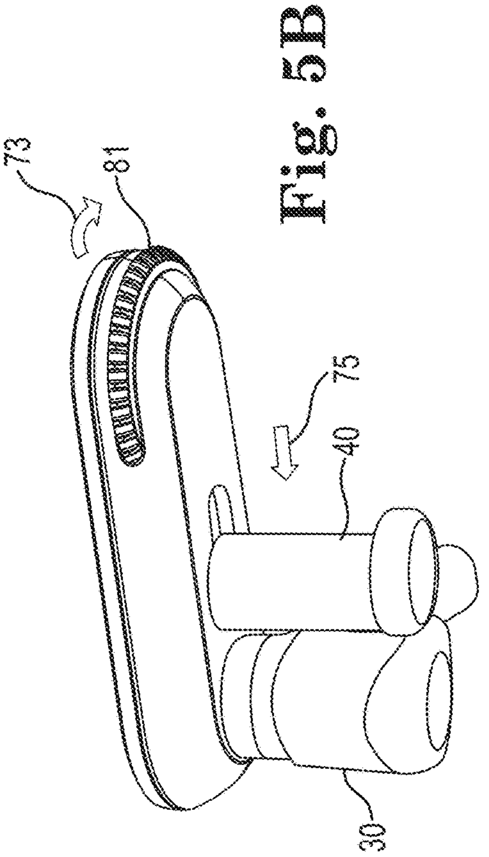
Figure 5C:
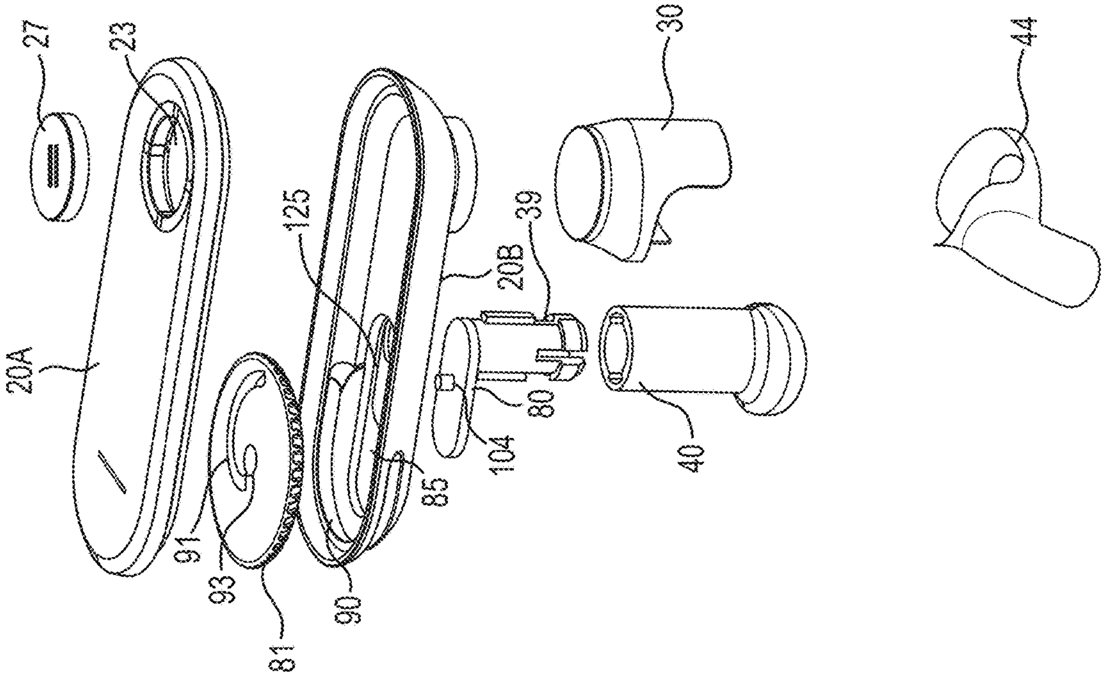

FIGS. 4A-4C are views of a third wearable device 12, while FIGS. 5A-5C are views of a fourth wearable device 13. The third wearable device 12 and the fourth wearable device 13 are analogous the first wearable device 10 with the change that the adjustment mechanism 81 and components associated therewith (e.g., in contact therewith) are different. For instance, FIGS. 4A-4C illustrate embodiments where the adjustment mechanism is manifested as a rotatable lever, while FIGS. 5A-5C illustrate embodiments where the adjustment mechanisms is manifested as a rotatable wheel. Hence, each of FIGS. 5A-5C illustrate embodiments wherein the adjustment mechanism is manifested as a rotatable adjustment mechanism.

The rotatable adjustment mechanisms may be rotatable, at least partially, about an annulus 93 and/or a peg 104 disposed in the annulus 93. The range of rotation may be anywhere from about 10 degrees to about 360 degrees. For instance, the rotatable lever illustrated in FIGS. 4A-4C and the rotatable wheel illustrated in FIG. 5A-5C may have a range of rotation that is in a range from about 10 to about 50 degrees. Each of the rotatable lever and the rotatable wheel may include a portion that is exposed from the housing 20 (e.g., a lever or a portion of the wheel) can is configured to be contacted by a user to impart rotation of the rotatably adjustment mechanism. That is, the housing 20 can include a slot or opening 90 at an end of the housing 20 that permits the wheel or the lever to protrude (e.g., in a substantially longitudinally direction) and extend a distance from the housing 20, while another portion of the adjustment mechanism 81 is disposed in the housing. For instance, the lever or a portion of the wheel can extend extending laterally through the slot 90 to a position outside of the housing 20, thereby permitting a user to actuate (rotate) the rotatable adjustment via contact with the lever or portion of the wheel outside of the housing 20.

As mentioned, the second extending structure 40 can be coupled to the carriage 80. As illustrated in FIGS. 4A-4C and 5A-5C, the carriage 80 of the third and fourth wearable devices 12, 13 can include an extended portion 39 configured to extend through an elongated aperture 125 formed in the second molded piece 20B of the housing 20. The extended portion 39 can be configured to be inserted in or around and otherwise be coupled to the second extending structure 40 e.g., via a friction fit or interference fit of tabs or ribs located on an end or other portion of the extended portion 39 within an opening in the second extending structure 40. These are merely examples, alternate or additional mechanisms of coupling the components herein are possible such as coupling components together via a first connector (e.g., male connector) associated with or integral with a first component and a second corresponding connector (e.g., a female connector) associated with or integral with a second component, via a latch and/or pin in conjunction with a corresponding aperture, etc. are possible.

Continuing with the description of FIGS. 4A-4C and 5A-5C, the portion of the adjustment mechanism 81 that is disposed within the housing can include a notched or tooth structure (e.g., notches 94 as illustrated in FIG. 4C) that is configured to interface with (interference fit with) a corresponding notched or tooth structure (e.g., notches 92 as illustrated in FIG. 4C) on the carriage 80. Hence, rotation of the rotatable lever or rotatable wheel in a given direction (e.g., in the direction 73) and be translated via the interface between the corresponding notched or tooth structures to impart longitudinal movement (e.g., in the direction 75) of the carriage 80. For instance, rotation of the wheel or lever in a first direction can impart movement of the carriage 80 longitudinally toward the first extending structure 30, while rotation of the wheel or lever in a second direction (opposing the first direction) can impart movement of the carriage 80 longitudinally away from the first extending structures 30. Thus, rotation of the lever or wheel permit a user to readily adjust that distance 31 between the first extending structure 30 and the second extending structure 40.

For instance, the lever can rotate from a first position (at a first end of the slot extending through the first end of the housing), as illustrated in FIG. 4A, to a second position at a second end of the slot extending through the first end of the housing 20 that is opposite the first end of the slot), as illustrated in FIG. 4B. Similarly, the wheel can include a curvilinear slot 91 extending within a portion of the wheel. In such instances, a first end or portion of another peg or projection element (not shown) can be disposed within the curvilinear slot 91 and a second end of the peg or projection can be fixable coupled to the housing 20 such that the peg or projection can limit the degree of rotation of the wheel. For instance, the wheel can be configured to move between a first position (where the peg or projection is located at a first end of the curvilinear slot), as illustrated in FIG. 5A, to a second position (where the peg or projection is located at a second end of the curvilinear slot opposite the first end of the curvilinear slot, as illustrated in FIG. 5B.

In some embodiments, a spring or other mechanism can disposition the carriage 80 of any one of the devices 10, 11, 12, or 13 to given position. When present, the dispositioning mechanism can be coupled to the carriage 80 or the adjustment mechanism. For instance, the dispositioning mechanism can be a spring that is directly coupled to the carriage 80 (e.g., having one end coupled to the carriage and another end coupled to the housing), among other possibilities. Similarly, in some embodiments the dispositioning mechanism can be a spring. The disposition mechanism (not shown) can be configured to disposition the carriage 80 to a longitudinally extended position or can be configured to disposition the carriage to a longitudinally contracted position.

In some embodiments, the carriage 80 can include an elongated slot 98 extending longitudinally along a portion of the length of the carriage 80. In such embodiments, a projection or peg can be configured to be slidably disposed within the elongated slot 98. For instance, the lower lid 20B can include an elongated peg 99 or other shaped protrusion configured to extend into the elongated longitudinal slot 98, as illustrated in FIG. 4C. The presence of the elongated slot 98 and the corresponding protrusion or elongated peg 99 can promote aspects herein such as ensuring that the carriage 80 is configured to translate in a substantially longitudinal direction within the housing 20.

Figure 6:
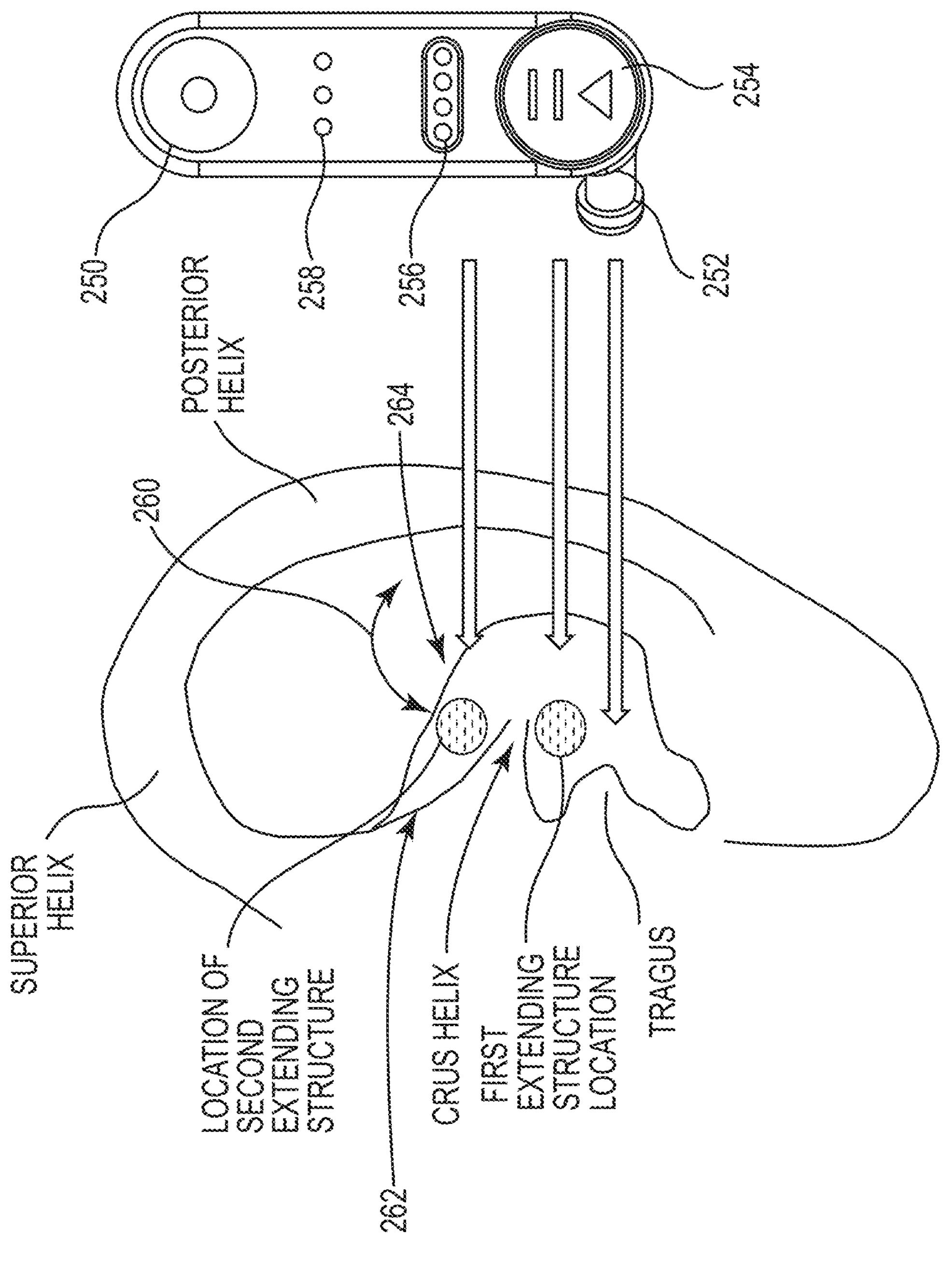
FIG. 6 illustrates placement of a wearable device.

FIG. 6 illustrates placement of a wearable device. The device 250 includes an anchor arm 252. A button 254 is provided for starting or stopping (e.g., pausing) an audio output of the device 250. A tap design, rather than button 254, may be used if desired. Indicator LEDs may be provided at 256 and/or 258. Alternatively, or in addition, the device 250 can include a battery status ring (e.g., the battery status ring 351 as illustrated in FIGS. 8A-8B and 9A-9B, herein). A speaker may be used to provide audible indications of status, such as by inclusion on the anchor arm 252 or elsewhere on the device. Alternatively, or in addition to the battery status ring and/or other controls or indicators depicted on the device 250, a separate device such as a smartphone, tablet, or laptop computer, etc. and/or a special purpose programmer or user device may be coupled in a wired or wireless manner to the device 250. This device may be configured with a software and/or firmware to communicate with the device 250. For instance, the device may be configured to control and/or monitor aspects of the device 250 such as starting, stopping, and/or otherwise modifying operation (e.g., audio output) of the device 250.

The device 250, with anchor arm 252, and an element such as a speaker, electrode, vibrating element and/or audio output device as in any of the preceding versions of a wearable device, will be placed as indicated by the arrows. The anchor arm 252 passes behind the tragus, and/or into the auditory canal. This brings the element such as a speaker to the position marked speaker location, and the second extending structure to the position marked second extending structure. Such positioning would also put the element such as the speaker on/at the conchae caverna, and the second extending structure on/at the conchae cymba. In other examples, the element may be differently placed, and/or more than one element can be used. Further, rather than or in addition to a given element such as a speaker, another type of element such as an electrode, a vibrating element, and/or a sensor such as those described herein may be used, as desired, singly or in combinations. Similarly, such positioning would put an element such as the first electrode on/at the conchae caverna, and other element such as the second electrode on/at the conchae cymba, in embodiments with such electrodes. In other examples, one or the other of the electrodes may be differently placed, and/or more than two electrodes can be used. Further, rather than electrodes, other vagus nerve stimulation elements may be used, as desired, singly or in combinations.

As indicated by line/arrow 260, in several examples the device may be positioned by inserting the anchor arm 252 into the auditory canal, and/or beneath the tragus, and then twisting the device. Some examples may twist the device in a superior/anterior direction, bringing the second extending structure (not shown) into a position abutting the anatomy of the exterior of the ear, such as a superior portion at the posterior edge of the crus helix, marked at 262. This positions the housing more vertically in the ear, with the end opposite the anchor arm 252 near the superior helix. Other examples twist in the opposite direction, in an inferior/posterior direction, bringing the second extending structure (again, not shown) into a position abutting the anatomy of the exterior of the ear, such as the antihelix, as indicated at 264. Whether the device is twisted or not, once placed within the ear, expansion of the extending structures creates force between portions of the boundary of the cavum (ear canal, tragus, and antitragus) against portions of the boundary of the cymba (helix, crus of helix, and antihelix) to secure the device within the ear.

This twisting step highlighted at 260 works the device into a desired position, and can be performed by the user in a simple, quick installation step. In some examples, no molding, curing or reshaping is needed. Because the second extending structure has a variable length, such as by including therein a resilient member or spring, such twisting allows the device to more or less automatically achieve a desirable position in which the electrodes, speakers, or sensor(s) are positioned against or proximate to the user's skin. An adhesive strip, such as tape or other substrate material, can be added if needed to maintain device positioning, however it is envisioned that an additional piece of tap will not be needed for most users, again simplifying the use of the system for the user.

Optionally, if a clip is used, the clip would pass over the helix, for example at a superior or posterior location, or elsewhere and/or in-between, to hold the device in place. Optionally, if tape is used, the tape may extend to and over the region marked superior helix, extend to and over the region marked posterior helix, or elsewhere.

Regardless of the optional clip or tape inclusion, the device 250, using the anchor arm 252 and the extending structures described herein, is configured for placement such that the entire device, in some examples, is positioned inside the periphery of the ear, with no wires extending therefrom. In other examples, a wire does extend out to a return electrode positioned elsewhere on the patient, such as the torso or neck, if desired. In some examples, only a single device 250 is present in the system, omitting a second device positioned on the other ear. In some examples, only a single device 250 is present in the system, omitting a second device positioned on the other ear. The device 250 may be configured for positioning on the left ear, as may be inferred from FIG. 6. Alternatively, the device may be configured for positioning on the right ear, if desired.

Some examples may include two devices 250 that are separately positioned, without mechanical/electrical contact therebetween, one for each ear of a user. For such as "two-device" system, audio output can be delivered independently by a respective speaker located in each device, in some examples. In other examples, may be coordinated such as by providing wireless communication circuitry in each device so that the two devices can communicate with one another to coordinate audio delivery, or so that each device can communicate with another device such as a user's smartphone (operating an application specific to the system) that communicates with each device to synchronize or coordinating audio delivery.

Figure 7:
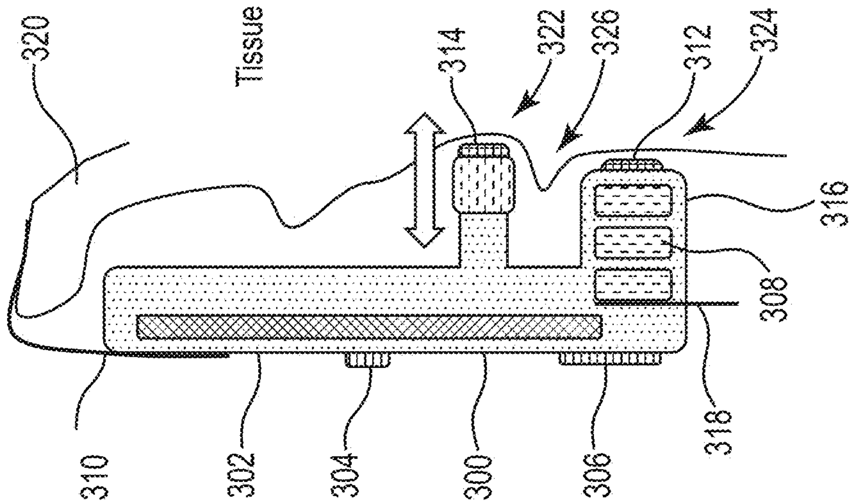
FIG. 7 is a side section view illustrating speaker positioning in the ear.

FIG. 7 is a side section views illustrating mechanisms for securing a wearable device to the ear. In FIG. 7, a device 300 is shown secured to the user's ear. Due to the capability of the devices herein to vary a length thereof (e.g., a variable length between the first and second extending members), in some embodiments the wearable devices herein can be secured to the user's ear in the absence of another element (e.g., tape or other type of additional element). However, in some embodiments, tape or another type of adhesive element can optionally be attached to the device 300 and the superior helix 320 to promote retention of the wearable device in the ear. In some embodiments, the device is sized and shaped so that when positioned as shown, the first extending structure 330 is positioned at the conchae caverna 324, and the second extending structure 340 rests against tissue at the conchae cymba 322. The positioning can also be characterized as having the first extending structure 330 and second extending structure 340 positioned on opposing sides of the crus of helix 326. For instance, the positioning can also be characterized as having the first electrode (represented as element 312) and the second electrode (represented as element 314) positioned on opposing sides of the crus of helix 326. As mentioned, the first extending structure 330, the second extending structure 340, or both, can include an audio output device. For instance, an element 314 such as a first electrode and/or a speaker can be located on or near an end of the second extending structure 340, as illustrated in FIG. 7. In some embodiments, the element 314 can be located on or near the end region the second extending structure 340 and another element 312 such as a second electrode and/or a sensor such as those described herein can be on or near the end of the first extending structure 330, as illustrated in FIG. 7. Alternatively or in addition, another audio output device (e.g., a speaker), another electrode, and/or another sensor can be located at a different location in the devices herein. Due to the capability of the devices herein to vary a length thereof, in some embodiments the wearable device can be secured to the ear without any of an additional anchor arm, clip, and adhesive tape. In such embodiments, the devices herein can be characterized in part by an absence of each of anchor arm (e.g., a C-shaped or other shaped protrusion configured to extend around a portion of an ear), clip, and adhesive tape.

Illustratively, and without limitation to a particular layout, the device 300 is shown having a printed circuit board 302 therein, coupled by feedthrough or other wires (not shown) to the alert indicators 304, on/off/pause button 306, first electrode or sensor 312 and a second electrode or an audio output device (e.g., speaker) 314. That is, in some embodiments, element 312 can be a first electrode and element 314 can be a second electrode. However, in some embodiments, element 312 can be a sensor and/or element 314 can be a an audio output device. A stack of battery cells 308, which may be standard button cells or may be a custom design, is contained in this example in the first extending structure 316. Other layouts and battery types can be used; any number of battery cells may be used, though it is expected generally that one to three cells would be used. The device may be a single use device (where single use means use for a single user for a limited period of time e.g., up to one month, or up to fifteen days, for example, and/or where single use indicates the batteries 308 are not replaceable). In other examples, the device may have rechargeable or replaceable batteries 308 and is adapted for repeated use. A removeable tab 318 may be used to preserve battery capacity prior to use; once the tab 318 is removed, the electrical circuit for powering the device is completed and the device electronics are enabled. In some examples, an optical light pipe such as an optical fiber may be used to transmit light from LEDs on the circuit board 302 to desired positions, for instance for use on the indicators.

Figure 9:
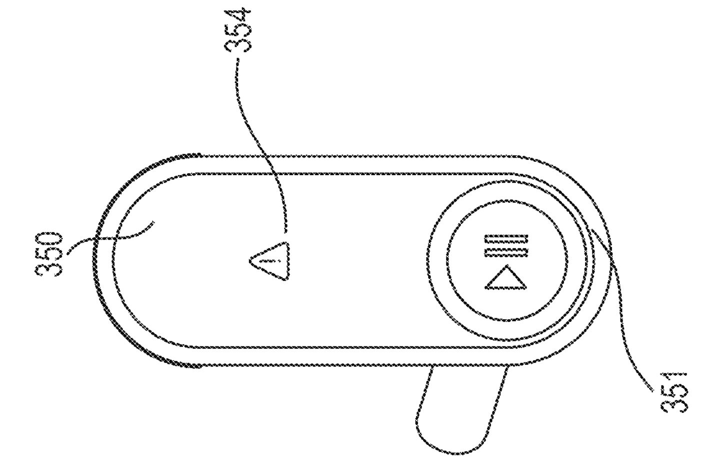
FIG. 9 shows an illustrative example of status and warning lights.
Figure 8:
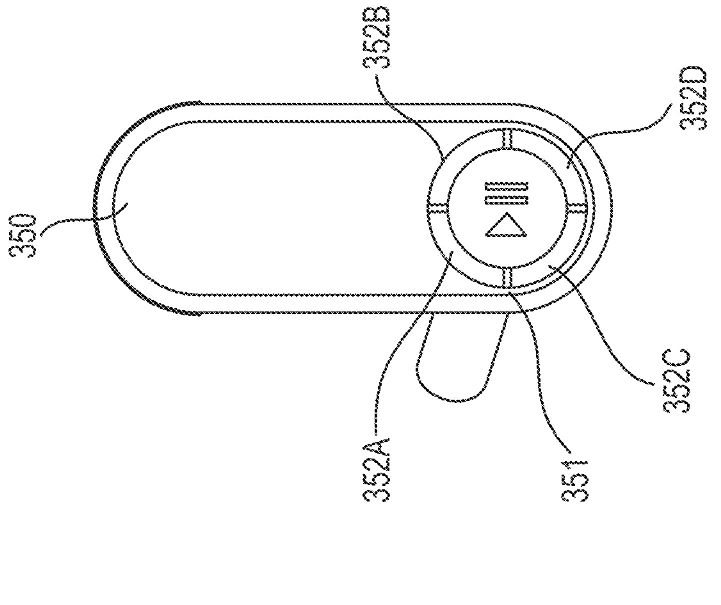
FIG. 8 shows an illustrative example of status and warning lights.

FIGS. 8-9 provides an illustrative example of status and warning lights. The illustrative device 350 can correspond to any of the devices 10, 11, 12, and/or 13 described herein. Alert indicators (lights typically) can include power indicators (e.g., on/off indicators), connectivity (e.g., WIFI® and/or BLUETOOTH®) indicators, and/or or a low battery alert 354.

Other alerts and mechanisms for interaction with the user may be used. A digital screen can be used if desired instead of discrete alert lights.

The multi-purpose light emitting diode ring 351 can be configured to indicate battery health or status and/or other aspects of device operation by illuminating, flashing, and/or turning off some or all the progress lights segments which comprise the ring. For instance, the multi-purpose light emitting diode ring 351 can be configured to incrementally indicate an incremental reduction in battery charge by flashing or illuminating an individual segment to indicate that corresponding battery charge level. For example, the multi-purpose light emitting diode ring 351 can be configured to incrementally indicate a battery charge level by turning off the individual segment corresponding to a range of battery charge levels (e.g., from 100 percent to 75 percent charged) responsive to the battery charge being reduced to a battery charge level (e.g., 73 percent0 that is less than the range of battery charge levels and flashing a subsequent individual segment to indicate that the battery charge level is within a subsequent (lower) battery charge level during a subsequent corresponding segment of time, as detailed herein. However, other mechanisms to indicate battery charge level and/or device status/operation (e.g., changing a color, varying an intensity, etc. of the status lights can be utilized alternatively or additional to indicate device status and/or battery charge level.

The multi-purpose light emitting diode ring 351 can be configured in a in a clock-like circular pattern to indicate battery charge level and/or can include device status indicators. For example, the progress ring can be formed of various segments representative of distinct portions or ranges of battery charge levels. For instance, as illustrated in FIGS. 8A-8B and 9A-9B the ring 351 can have four light segments 352A, 352B, 352C, 352D (collectively referred to herein as light segments 352). The light segments 352 can correspond to a range of respective battery charge levels (e.g., each segment corresponds to a about 25 percent of an overall battery charge level). A liquid crystal display, touch-screen, or other display may be used instead of the ring 351, if desired.

As illustrated in FIGS. 8-9, the device 350 can include one or more alert lights that can be selectively displayed or illuminated. Alert lights may include, for example, lights that indicate problems with the device, which may include poor contact with the skin (determined for example using a temperature sensor or an impedance monitor, as desired) when the device includes a sensor such as the sensor 312 in FIG. 7, expiration of the device, other failure in the device, low battery, etc. A button may be used to initiate or pause the audio output, as desired. As illustrated in FIGS. 8-9, the status ring 351, the light segments 352, and/or the alert lights 354 can be located on an exterior surface (e.g., an exterior surface of the first molded piece 20A, as described herein) of the device 350. Having the status ring 351, the light segments 352, and/or the alert lights 354 be located on the exterior surface of the device can promote aspects herein such as permitting access to and/or permitting the status ring 351, the light segments 352, and/or the alert lights 354 to be readily viewed (e.g., be visible) even when the device is positioned in in an ear of a user). However, the quantity, the type, and/or the location of the status ring 351, the light segments 352, and/or the alert lights 354 can be varied.

Figure 10:
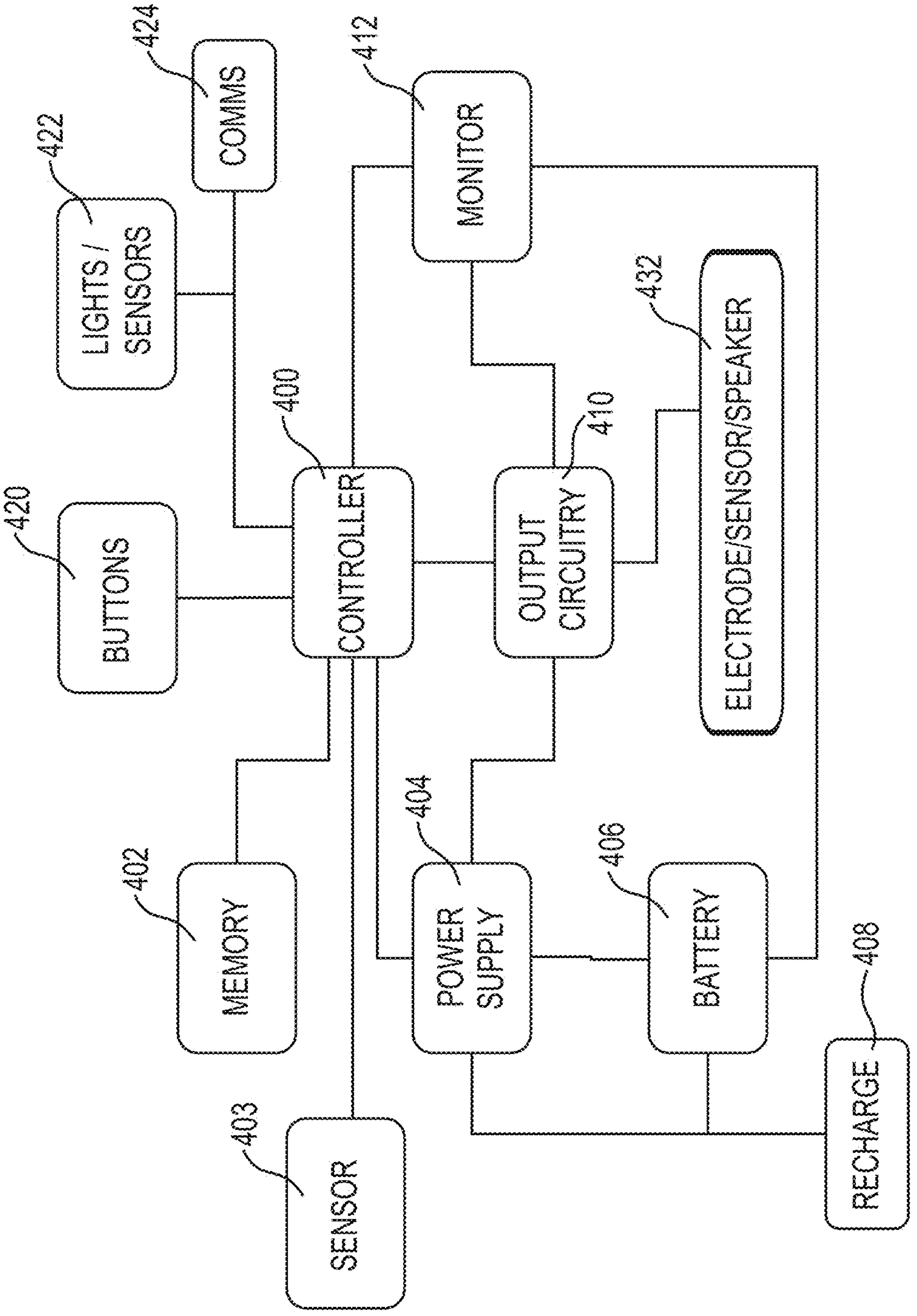
FIG. 10 is a block diagram for illustrative circuitry.

FIG. 10 is a block diagram for illustrative circuitry. The illustrative circuitry may be described as operational circuitry for the device, and would be contained in the housing as shown in any of the preceding examples. The device includes a controller 400. The controller 400 may take many forms, including, for example, a microcontroller or microprocessor, coupled to a memory 402 storing readable instructions for performing methods as described herein, as well as providing configuration of the controller for the various examples that follow. The controller 400 may include one more application-specific integrated circuits (ASIC) to provide additional or specialized functionality, such as, without limitation, a signal processing ASIC that can filter received signals from a sensor 403 such as those described herein using digital filtering techniques. Logic circuitry, state machines, and discrete or integrated circuit components may be included as well. A controller 400 may take the form of a state machine, if desired. The skilled person will recognize many different hardware implementations are available for a controller. Likewise, the memory 402 can take any suitable form, including Flash memory, combinations of multiple memory types, etc.

The operational circuitry also includes a power supply block 404, coupled to a battery 406. The power supply block may include voltage step-up or step-down circuitry, or may include appropriate regulators, converters and the like, as well as smoothing circuitry as needed/desired to obtain power from a battery 406 and provide power at specified voltage/current for use in the controller 400 as well as the output circuitry shown at 410. One, two, three, four or more battery cells may form a battery 406; commercial off-the shelf button-type batteries may be used, or specialized versions may be developed and used. For example, three or four lithium-chemistry button batteries may provide 9 or 12 volts of power supply, allowing maximum currents in the device to stay relatively small (reducing heat), while generating sufficient headroom to provide desired current or voltage levels for therapy. Batteries may be replaceable, if desired. Rechargeable batteries could be used, whether removeable and rechargeable or by providing a recharging circuit as indicated at 408, in the device, where power can be transferred to a recharging circuit by use of an electrical port on the device, or by wireless transmission (inductive, RF, ultrasonic, etc.) to a transducer on or inside the device. An example may use an inductive loop coupled to a rectification circuit that in turn delivers current/power to the battery 406 for recharging, for example. A recharging case or cord, for example, can be used to enable recharging of the device or devices. Some examples may include electrical contacts on the device for recharging in a recharging case/housing, if desired.

The power supply 404 may further include a dedicated voltage converter to provide, for example, a source for a current controlled output circuitry. In an example, an inductive or capacitive step-up circuit is used to store a 60-volt amplitude on one or more capacitors to provide headroom for a current controller output circuit using, for example, one or more current mirrors to control the output current. Suitable amplifier-based circuits may be used, instead, or any other desired circuit can be used. While inductive step-up circuitry can be used, capacitive converter designs may provide better MRI-compatibility and tend to be smaller and introduce less weight.

The output circuitry 410 may include a set of switches, such as an H-Bridge circuitry design, configured to provide alternating signal outputs. Square wave outputs may be used, and may be current controlled or voltage controlled, as desired. Non-square waves can be used as well, such as exponentially decaying, sinusoidal (in which case a resonant circuit can be included), triangle, ramped, etc. The power supply 404 is configured to provide voltage step-up (such as a voltage multiplier using inducive or capacitive elements), allowing the output circuitry to shape and control the power signals issued to the electrode, sensor, and/or transducer 432 such as those described herein. The electrode, sensor, and/or transducer 432 may also receive control signals from the controller 400 to manage, for example, output frequency of the transducer, depending on design.

The monitoring circuitry 412 can include one or more sensors such as those described herein. For example, the monitoring circuitry can be manifested as a temperature sensor (such as a thermistor, resistance temperature detectors, thermocouples, and/or integrated circuit sensors) to monitor temperature at the tissue interface.

The monitoring circuitry 412 may also monitor battery status, including, for example, a current sensor or coulomb counter if desired to track actual battery use, or a voltage sensor to determine open, lightly loaded, or loaded output voltage of the battery 406 or individual cells therein. Battery usage may instead be tracked, for the purpose of determining battery end of life/status, by the controller 400 using timers, etc., as desired.

The memory 402 may store controller-readable instructions for operating the device in any suitable form, and can also store operating data, including time spent in pause, on/off or other operational data. Operational data may include temperature or impedance data, if desired, or any other sensed parameters or signal.

The controller is also coupled to what may be termed input-output devices, including any buttons 420 on the device, sensors, and/or lights 422 described herein. A screen or touchscreen may be used instead or as well as those items shown. Some systems may optionally include an RF circuit block 424, including, for example and without limitation, BLUETOOTH®, WIFI®, and/or any wireless communications circuitry (antenna, driver, crystal/resonator, etc.) for performing wireless communication with a separate device. For example, a smartphone operating an application may communicate via Bluetooth with the device to control any characteristic of device operation (duration, on/off, repetition rate, amplitude, pulse width, type, etc.) and/or to obtain device operational data (usage, battery status, etc.).

General purpose devices may communicate with the system if desired, using for example an application operating on a smartphone, tablet, or computer.

Communication may be used to modify settings, upload new software to the device, and/or to download device and/or application usage data or other usage data. Device status, such as battery capacity, may be communicated. Communication may also be used to turn the device on or off, if desired, rather than relying on a button or other actuatable component on the device and/or device housing.

Figure 11:
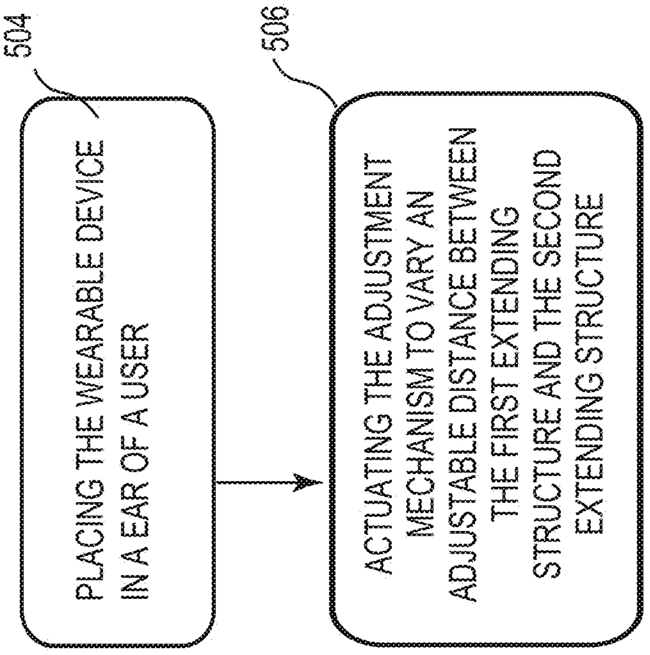
FIG. 11 shows a block process flow diagram of an illustrative method.

FIG. 11 shows a block process flow diagram of an illustrative method. A relatively comprehensive method is shown; some other or alternative examples may omit one or more blocks/steps, or may replace the illustrative steps shown with other steps. For instance, the methods herein can additional include adjusting the actuating the adjustment mechanisms to vary an adjustable distance between the first extending structure and the second extending structure until the second extending structure abuts the helix, the antihelix, the inferior crus, or any combination thereof, as described herein. For example, the method can include placing the anchor arm in the auditory canal or at least partially beneath the tragus, as indicated at 504. Further, the methods herein can include adjusting the adjustable distance prior to, during, and/or subsequent to placing the devices (e.g., an anchor arm of the devices) in the auditory canal. For example, the adjustment can be performed subsequently to placing the anchor arm in the auditory canal or at least partially beneath the tragus. As mentioned, the adjustment mechanisms herein can be actuated with one or more digits on an individual hand of a user, as indicated at 506. Hence, the adjustment mechanisms herein can permit adjustment with one hand (an individual) hand of a user. The adjustment can be performed by way of rotation or translation of the adjustment mechanism e.g., relative to the housing 20, unlike some device that require pinching or the use of two hands to adjust aspects of a device.

Figure 12:
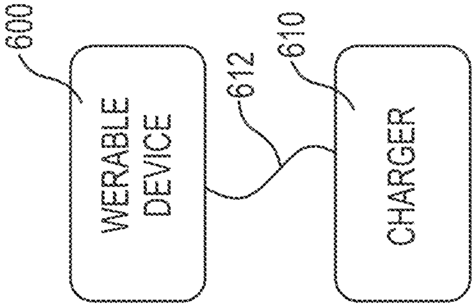
FIGS. 12-13 illustrate wearable devices and charging systems.
Figure 13:
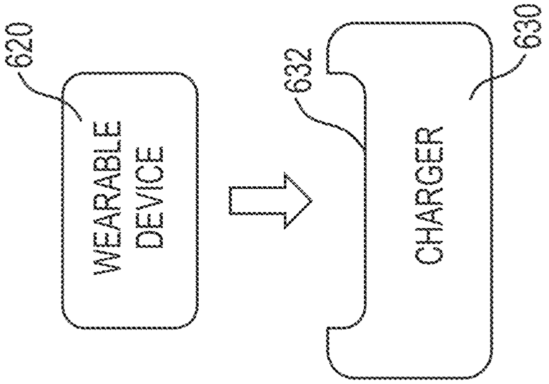

FIGS. 12-13 show wearable devices with chargers. For a user to use a device in a long-term sense, the power supply must be either replaceable (such as with replaceable batteries) or replenishable. A rechargeable wearable device may be useful in any context. In FIG. 12, a wearable device 600 is shown connected to a charger 610 using a wire 612. The connection may use standard connectors, such as uniform serial bus (USB) connectors, micro-USB, etc., or may be a special purpose connector 612 to prevent unauthorized use or modification of the wearable device 600, if desired. The charger 610 may be battery powered or may use wall power, as desired. The wearable device 600 may remain positioned in the ear of a user during charging, or may be removed. Another example is shown at FIG. 13. Here the wearable device 620 is received in a charger 630, having a depression or cradle 632 for receiving the wearable device 620. Electrical connectors can be provided in the cradle 632, positioned to align with electrical connections on the outside of the wearable device 620. Other modes of power transmission can be used, including inductive, RF, optical, etc., as desired.

In each of FIGS. 12-13, data transmission can be performed while charging takes place. For example, firmware in the wearable devices 600, 620 may be updated, or settings modified, as desired. The chargers 610, 630 may be connectable to additional devices, such as a smartphone operating a dedicated application for the purpose of software updating, and/or wearable device operation modification, if desired.

Figure 14:
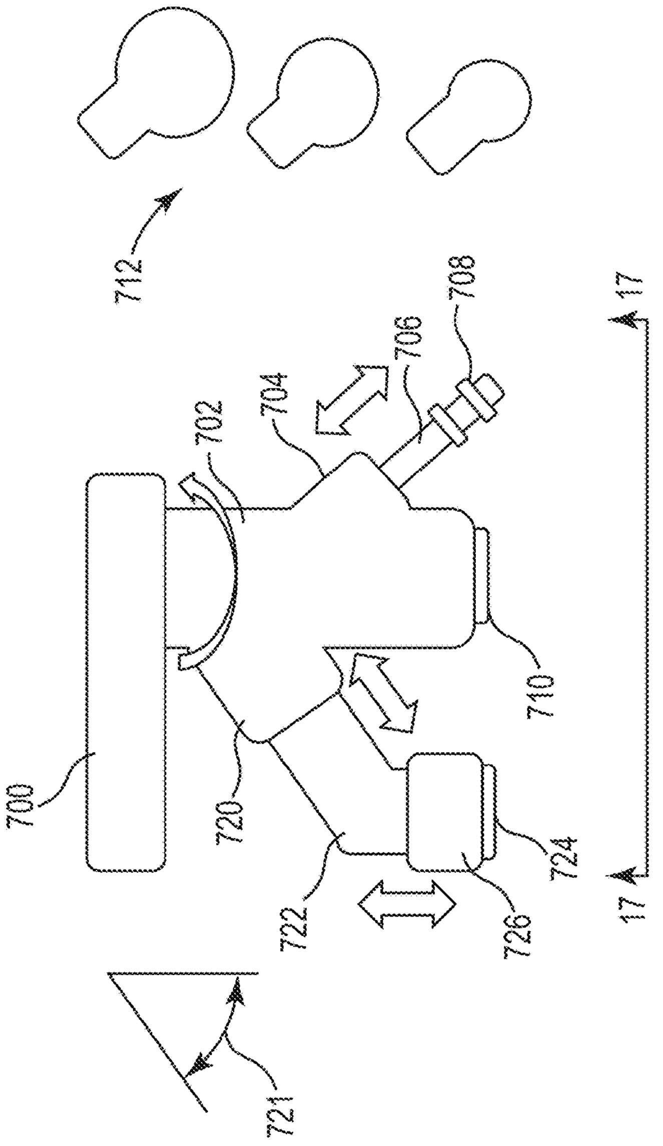
FIGS. 14-15 illustrate further alternative designs for wearable devices.
Figure 15:
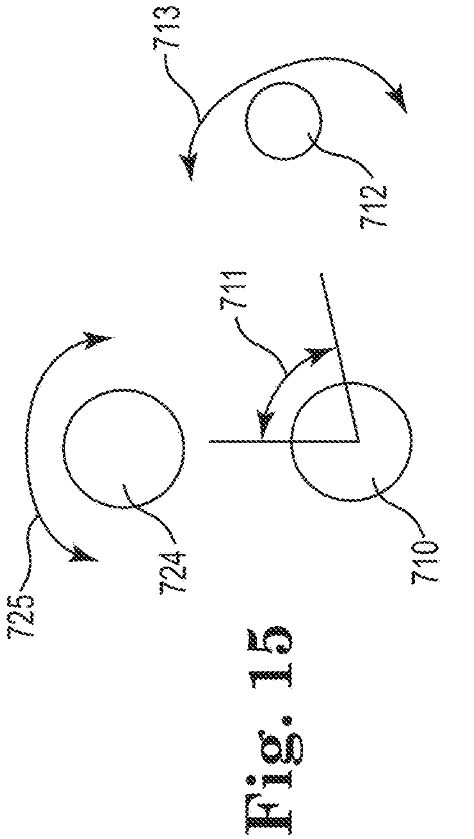

FIGS. 14-15 illustrate further structures. In FIG. 14, a wearable device 700 includes an extending structure 702 which carries an anchor arm 704, having an extending anchor arm 706 moveably mounted therein as indicated by the arrow. Ridges are provided as shown at 708 for holding a removable tip thereon, to anchor in the auditory canal of the user's ear. A speaker is represented by element 710. When the device is placed in an ear, the speaker 710 may be placed in or adjacent to the auditory canal of a user. A plurality of tips 712, in a range of sizes if desired, are provided with the device. Tips 712 may come in various shapes or sizes to allow different users to select a best fit. Tips 712 may be replaceable, as the position in the auditory canal may lead to wax build up, for example, making occasional or periodic replacement useful.

The extending structure 702 also carries an extension 722 which can be extended or retracted relative to a receiver 720, such as by including a spring-loaded structure, as indicated by the arrow. The extension 722 forms an angle 721 relative to the axis of the extending structure 702, the angle being, illustratively, in the range of about 30 to about 60 degrees; in an example, the angle 721 is about 45 degrees. An optional speaker or sensor 724 is positioned on a carrier 726, which may be a generally hollow piece that can slide over the extension 722, as indicated by the arrow. Positioning may again be spring loaded, if desired. This design has a single extending structure 702 relative to the main body of the device 700.

The extending structure 702 may be rotatable (at least partly) if desired, allowing the main body to directed, vertically, horizonal, or at an angle therebetween when placed on the user. For example, if a user is in a recumbent position the rotation of the extending structure may be used to adjust for comfort and secure positioning. In some examples, the receiver 720 is rotatable relative to the anchor arm 704, for example, allowing different angles to be defined therebetween, if desired.

FIG. 15 shows the orientation of speakers or sensors of FIG. 14. It may be noted that FIG. 14 illustrates the location of the anchor arm 706 relative to the extension 722 at an angle so that the extension 722 can be observed in one drawing. FIG. 15 illustrates these angles with a bit more clarity. The speaker 710, along with the optional sensor 724 and the anchor arm at tip 712 form an angle as shown at 711. The positions of speaker 724 and tip 712 are adjustable as illustrated with arcs 713 and 725, so that the angle 711 can be varied in the range of about 60 degrees to about 135 degrees, or more or less. The angle 711 may be, for example, about 90 degrees, if desired. The angle 711 can be adjustable if desired. In some examples, angle 711 is instead a fixed angle.

In some examples, textured, ridged, disk, or bulbous shapes (or combinations thereof) may be used to aid in securing the device in place by including such shapes on the anchor and/or an extending structure. For example, the three elements 710, 712, and 724 shown in FIG. 15 each represent touch points to tissue of a user. Any one, two or all three of these touch points can include a shape (such as bulbous or disk-shape), ridges, texture or roughening that discourages or prevents passage along or past tissue or a tissue ridge or layer, such as the helix, antihelix, helical crus, intertragal notch, tragus, and/or anti-tragus. Such shape, ridges, texture or roughening may be applied on all sides of any of the three touch points, or only along an outer edge or tissue-contacting side thereof, as desired. By outer edge, the intent is to indicate the portion of any anchor or extending structure that would press against tissue to hold the device in a desired position.

Figure 16:
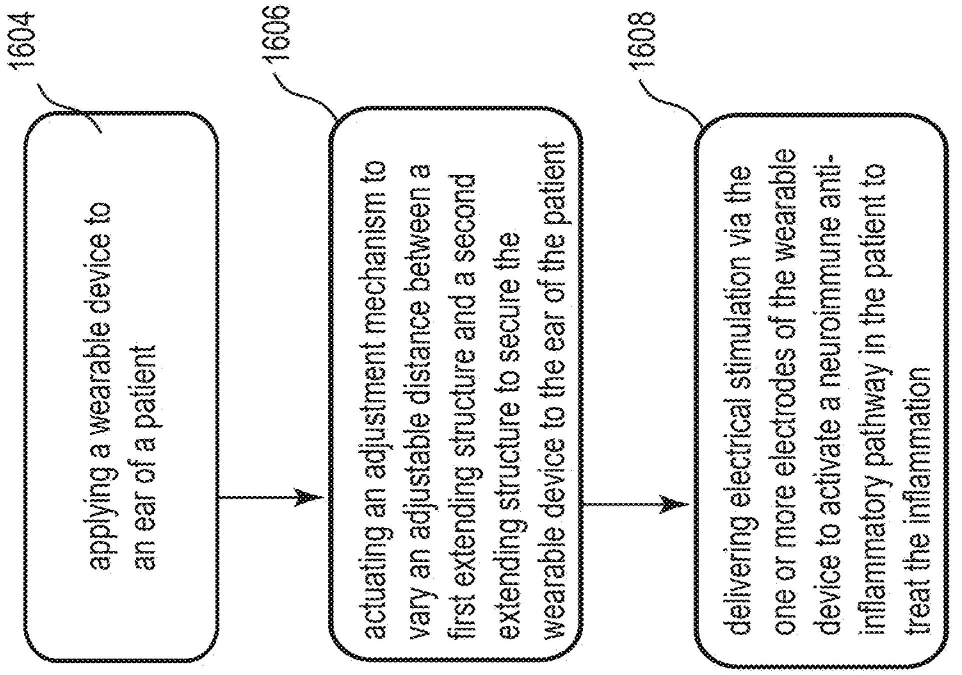
FIG. 16 shows a block process flow diagram of an illustrative method for treating inflammation.

FIG. 16 shows a block process flow diagram of an illustrative method for treating inflammation. The method for treating inflammation can be performed with the devices described herein including those that include at least one electrode, at least one vibrating element (e.g. a piezoelectric actuator), or a combination of one or more electrodes and one or more vibrating elements.

At 602, the method can include applying a wearable device to an ear of the patient. In some embodiments, applying the wearable device to the ear of the patient can include placing the wearable device in (in direct contact with) the ear of the patient, as detailed herein.

As mentioned, in some embodiments the wearable device can be placed in the ear of the patient without a clip and/or without an adhesive. The wearable device can desirably be adjusted to securely fit within a ear of a user, as detailed herein. For instance, at 606, the method can include actuating the adjustment mechanism to vary an adjustable distance between the first extending structure and the second extending structure to secure the wearable device to the ear of the patient, as detailed herein.

At 608, the method can include delivering electrical stimulation via the one or more electrodes of the wearable device. For instance, the electrical stimulation can be delivered to activate a neuroimmune anti-inflammatory pathway in the patient to treat the inflammation. In some embodiments, the stimulation can additionally or alternatively include delivery of oscillations provided via one or more vibrating elements.

In some embodiments, the electrical stimulation can be delivered delivering the electrical stimulation at a current amplitude in a range of about 0.1 mA to about 20 mA, a pulse width in a range of about 10 microseconds to about 20 milliseconds, and/or a frequency in a range of about 1 Hz to about 200 Hz. For instance, the electrical stimulation can be delivered delivering the electrical stimulation at a current amplitude in a range of about 0.1 mA to about 20 mA, a pulse width in a range of about 10 microseconds to about 20 milliseconds, and a frequency in a range of about 1 Hz to about 200 Hz. In some embodiments, the electrical stimulation delivered can be tailored to treat one or more particular types of inflammation. Examples of types of inflammation include inflammation that is associated with one or more conditions selected from the group consisting of: cerebrovascular disorders including stroke and post-stroke inflammatory response; metabolic disorders including diabetes mellitus and glycemic control disorders; drug-induced inflammatory responses including diabetes drug therapy complications; rheumatoid arthritis; inflammatory bowel disease; Alzheimer's disease, Crohn's disease; ulcerative colitis; multiple sclerosis; psoriatic arthritis; osteoarthritis; psoriasis; chronic inflammatory symptoms; and chronic fatigue syndrome.

The device and system may be configured for a variety of use cases. For example, the wearable vagus nerve stimulation can be used in conjunction with pharmacological interventions to treat sepsis in ICU patients. By targeting inflammation including use of vagus nerve stimulation, the system can help modulate the immune response and potentially improve outcomes in patients with severe sepsis.

In another example, in patients with acute respiratory distress syndrome (ARDS) in the hospital setting, wearable vagus nerve stimulation can be utilized alongside mechanical ventilation and anti-inflammatory medications to reduce lung inflammation and improve oxygenation. This combined approach may enhance the overall management of ARDS and potentially speed up the recovery process.

In another example, for patients with severe pneumonia requiring intensive care, wearable vagus nerve stimulation can complement antibiotic therapy and respiratory support by targeting systemic inflammation. By regulating the inflammatory response, this adjunctive therapy may help in reducing the severity of pneumonia and preventing complications in critically ill patients.

In another example, in the management of inflammatory bowel disease (IBD) exacerbations in hospitalized patients, wearable vagus nerve stimulation can be used along with corticosteroids and immunosuppressants to control intestinal inflammation. This combined treatment approach may offer a novel strategy to alleviate symptoms and promote mucosal healing in patients with severe IBD flares.

In another example, wearable vagus nerve stimulation can be combined with pain management techniques in post-operative ICU patients to mitigate surgical inflammation and improve recovery outcomes. By targeting the inflammatory cascade, this adjunct therapy may aid in reducing post-operative complications and enhancing the overall healing process in critically ill surgical patients. In addition, again for the post-surgery context, wearable vagus nerve stimulation can be utilized post-operatively to enhance bowel motility by delivering targeted electrical impulses to the vagus nerve, promoting gastrointestinal motility and reducing the risk of post-operative ileus.

In another example, a wearable vagus nerve stimulation device can be used in conjunction with remote monitoring systems to continuously track the patient's heart rate, blood pressure, and other vital signs. By integrating real-time data from the device with the digital monitoring platform, health-care providers can quickly identify any signs of worsening heart failure and intervene promptly to prevent readmission.

In an example, wearable vagus nerve stimulation can be used in combination with traditional pharmacological treatments for Congestive Heart Failure (CHF) to reduce readmission rates. By incorporating vagus nerve stimulation into the patient's treatment plan, the device can potentially improve heart function, reduce inflammation, and enhance autonomic balance, leading to better overall outcomes and decreased risk of hospital readmission.

In another example, wearable vagus nerve stimulation can be used exclusively for mitigation of pain related to medical intervention or medical conditions. Such medical interventions may include, but are not limited to, surgical procedures such as orthopedic surgeries (joint replacements, arthroscopic procedures, spinal fusion), cardiac interventions (bypass surgery, valve replacement, catheter-based procedures), abdominal surgeries (laparoscopic procedures, appendectomy, hernia repair), dental and oral surgeries, cosmetic and reconstructive procedures, neurosurgical interventions, and minimally invasive procedures including endoscopies, colonoscopies, and bronchoscopies. Additionally, the system may be employed during medical treatments such as chemotherapy administration, radiation therapy, injection-based therapies, tissue biopsies, wound debridement, and physical rehabilitation procedures. The wearable vagus nerve stimulation device may also provide therapeutic benefit for pain associated with medical conditions characterized by inflammatory processes, including but not limited to rheumatoid arthritis, osteoarthritis, inflammatory bowel disease (Crohn's disease, ulcerative colitis), fibromyalgia, neuropathic pain syndromes, autoimmune disorders (lupus, multiple sclerosis), chronic regional pain syndrome, temporomandibular joint disorders, chronic headache and migraine conditions, post-surgical chronic pain, cancer-related pain, and chronic low back pain, where the anti-inflammatory effects of vagus nerve stimulation may reduce both local and systemic inflammatory mediators contributing to pain perception and tissue sensitization.

In another example, wearable vagus nerve stimulation can be used exclusively for mitigation of stress-related hyperglycemia associated with medical intervention or medical conditions. Such medical interventions may include, but are not limited to, surgical procedures such as cardiac surgery (coronary artery bypass, valve replacement), major abdominal surgeries (liver resection, pancreaticoduodenectomy, bowel resection), orthopedic procedures (joint replacement, spinal surgery), neurosurgical interventions (craniotomy, tumor resection), trauma surgery, organ transplantation procedures, and emergency surgical interventions.

Additionally, the system may be employed during acute medical treatments such as intensive care unit admissions, mechanical ventilation, hemodialysis, chemotherapy infusion, radiation therapy, invasive diagnostic procedures (cardiac catheterization, bronchoscopy), burn treatment, and critical illness management where physiological stress responses elevate blood glucose levels. The wearable vagus nerve stimulation device may also provide therapeutic benefit for stress-related hyperglycemia associated with medical conditions including diabetes mellitus (both Type 1 and Type 2), prediabetic conditions, metabolic syndrome, acute myocardial infarction, stroke, sepsis, acute pancreatitis, chronic kidney disease, liver cirrhosis, chronic obstructive pulmonary disease exacerbations, psychiatric disorders with associated metabolic dysfunction (depression, anxiety disorders, post-traumatic stress disorder), chronic pain syndromes, sleep disorders, and endocrine disorders (Cushing's syndrome, hyperthyroidism), where vagus nerve stimulation may enhance parasympathetic tone, improve insulin sensitivity, reduce cortisol release, and modulate the stress-induced activation of the hypothalamic-pituitary-adrenal axis that contributes to elevated blood glucose levels.

Figure 17A:
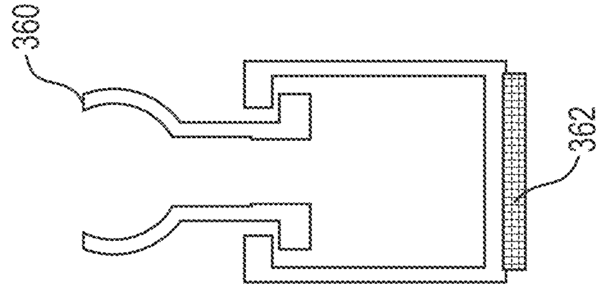
FIGS. 17A-17G show illustrative stimulation device designs.
Figure 17B:
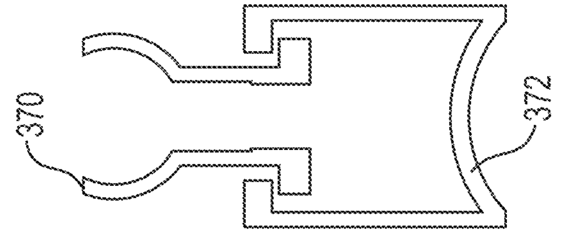
Figure 17C:
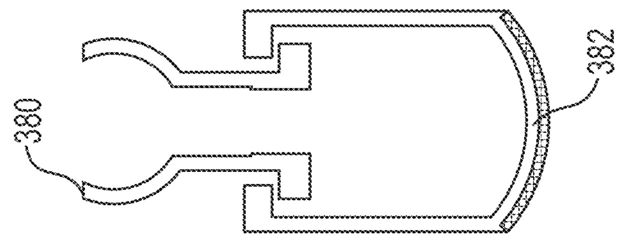

FIGS. 17A-17G show illustrative stimulation device designs. FIG. 17A shows an electrode assembly at 360, having a flat contact surface on which a hydrogel or other tissue coupling element 362 is provided. An adhesive, for example, may attach the coupling element 362 to the electrode assembly 360. FIG. 17B shows an alternative 370 with a concave contact region 372, which may help hold/contain the tissue coupling element and/or a hydrogel or other gel for aiding in signal transmission across the tissue-stimulation element interface. In some instances, an electrode may have a surface that is textured, roughened, scored, or dimpled to increase effective surface area, to thereby lower impedance, in addition serving to receive or retain coupling material, gel, and/or adhesive. Not only electrodes, but any of the described vagus nerve stimulating elements may have textured, roughened, scored or dimpled surfaces, or may comprise an adhesive layer, or may receive a piece of coupling material, gel or adhesive thereon. FIG. 17C shows an alternative 380 having a convex contact surface 382.

Figure 17D:
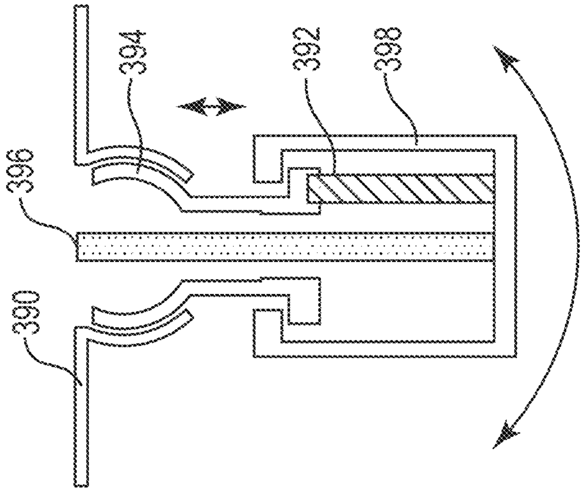

FIG. 17D highlights two different ways that the electrode 398 contact can be made adjustable. A spring or other resilient member 392 or 396 can be used to maintain pressure against the tissue once the device 390 is placed. The resilient member 392 or 396 may be, for example, a coiled spring, a compressible foam, or any other suitable structure able to be compressed and expand after removal of applied force. A swivel or ball-joint structure shown at 394 can allow the electrode to be laterally angled as desired. The resilient member shown at 392 presses against the end of the swivel or ball-joint structure 394; alternatively, the resilient member 396 may be used instead and is shown extending up to the device enclosure, for example, all the way to the circuit board, on which an electrical connection can be made so that resilient member 396 serves also as the electrical contact to the electrode 398.

Figure 17E:
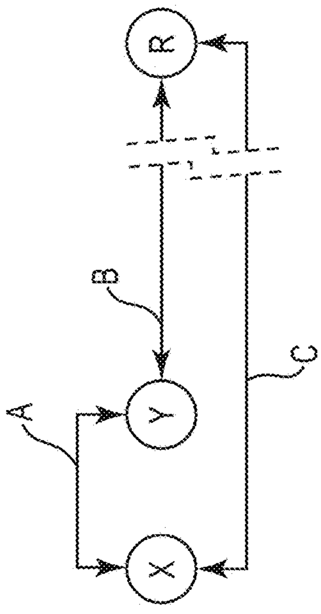
Figure 17F:
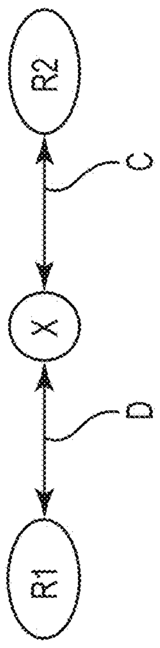

FIG. 17E illustrates different approaches to delivery of electrical stimulation. An electrical output requires at least two "poles" for delivery. A bipolar delivery occurs between two relatively closely spaced electrodes. For example, some of the designs shown above include first and second electrodes disposed, respectively, on the conchae caverna and conchae cymba; when electrical signal passes between two such electrodes, a bipolar output is generated. Line A, between electrodes X and Y in FIG. 17E can be understood as indicating a bipolar output. On the other hand, a monopolar delivery occurs between a first electrode positioned at a therapy site, and a remote electrode located away from the therapy target. Lines B (between electrode Y and a remote electrode, R) and C (between electrode X and a remote electrode, R) indicate monopolar therapy combinations. Multiple return electrodes can be used, for example to influence voltage fields and spread, focus or steer the outputs, such as shown in FIG. 17F where electrode X issues a therapy output with two return electrodes. The return electrode in FIGS. 17E and 17F may be positioned at any desired distance, as indicated with the use of the broken line gaps. Each of these different types of therapy may be used in various examples. Some examples will omit the remote electrode, R.

Figure 17G:
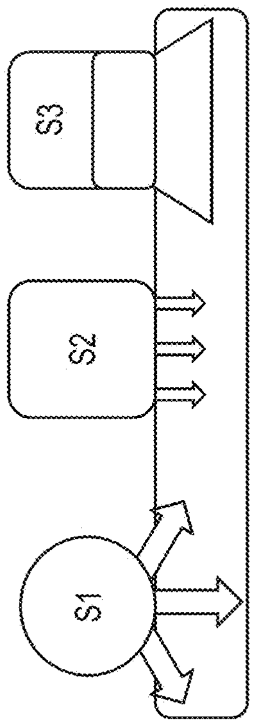

Other therapy modalities may not require paired neural stimulation elements. For example, as indicated in FIG. 17G, some stimulation elements, such as S1, can generate output stimulation that travels in a range of directions. Vibration/acoustic stimulation via a vibration element such as a vibration element located on the first anchor arm, the second anchor arm, or both, as well as magnetic stimulation, may travel in this way, such that S1 may be understood as an electro-mechanical, or electro-magnetic transducer. Thermal therapy can be generated as well, and so S1 may instead be a thermal element such as a resistor that converts electrical current to heat. Some optical outputs provide collimated light outputs, such as light emitting diodes and/or vertical cavity surface emitting lasers, as illustrated at S2. A dispersing lens may be included as shown for S3, to provide a spread the output light energy; alternatively, a less directional light source can be used, as desired.

Figure 18:
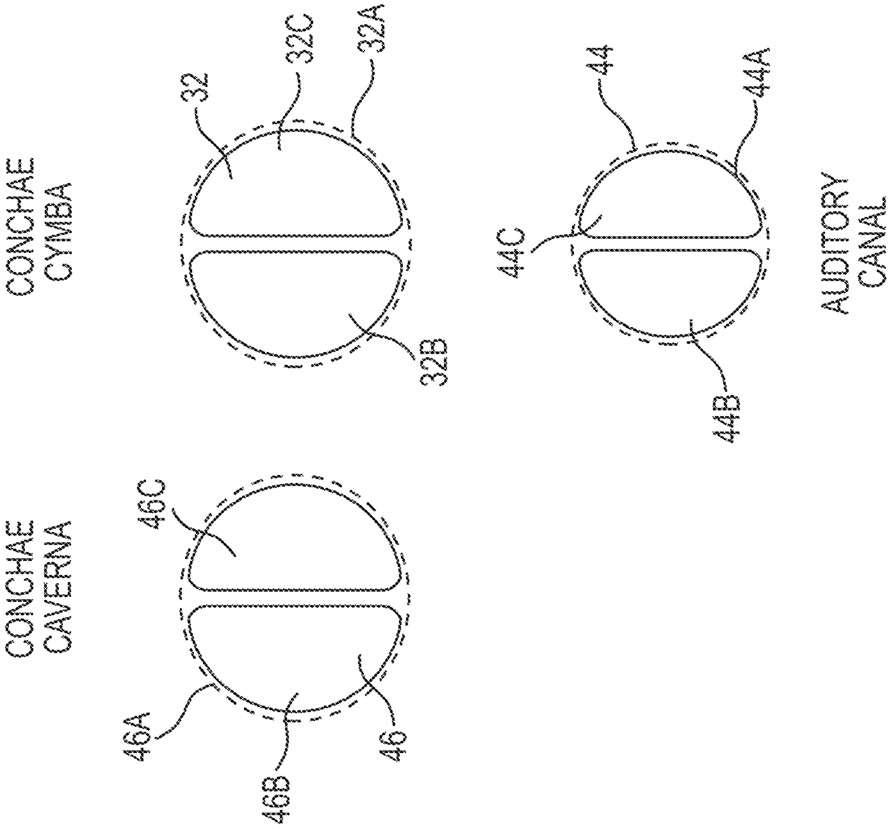
FIG. 18 illustrates various electrode configurations.

FIG. 18 illustrates various electrode configurations that can be used, as desired. Electrode structures are shown at 32, 44, and 46, corresponding to the electrodes that can be used in systems and devices herein. Various examples of system electrode configurations may be achieved. Electrode structure 44 would be positioned on the anchor arm, and is omitted in some examples. The electrode structure 32 may be a single electrode 32*a*, or may include more than one electrode, such as electrodes 32*b*, 32*c* (more than two may be used, if desired). Likewise, the electrode structure 46 may be a single electrode 46*a*, or may include more than one electrode, such as electrodes 46*b*, 46*c* (more than two may be used, if desired). When present, the electrode structure 44 may be a single electrode 44*a*, or may include more than one electrode, such as electrodes 44*b*, 44*c* (more than two may be used, if desired). Various combinations are contemplated:

Electrode structure 32 may include two electrodes 32*b*, 32*c*, with therapy delivered between those two electrodes 32*b*, 32*c* only, directing therapy to the conchae cymba. Other electrodes may be omitted, or may be present but inactive, or may delivered a separate waveform. Electrode structure 46 may include two electrodes 46*b*, 46*c*, with therapy delivered between those two electrodes 46*b*, 46*c* only, directing therapy to the conchae caverna. Other electrodes may be omitted, or may be present but inactive, or may delivered a separate waveform.

Each of electrodes 32*b*, 32*c*, 46*b*, 46*c* may be included in some examples, and therapy may be delivered in sequential anode/cathode pairs, for example as shown here:

| Anode | Cathode |
|---|---|
| 32b | 46b |
| 32c | 46b |
| 32b | 46c |
| 32c | 46c |

Therapy may start at the top row and proceed to each successive row. After one round of such therapy, the sequence may be repeated with opposite polarity, for example. Other combinations and/or sequences can be used. As the skilled person will understand, this approach may require multiple sources in the electronics of the device, providing multiple, independent signals to control individual electrodes. Some other examples may have one electrical source and a plurality of switches to direct therapy signals as desired. Some examples may have multiple electrical signal sources and a set of switches arranged to multi-plex the output signals as desired.

With a larger number of electrodes, additional flexibility is enabled allowing the electrical field applied to the underlying tissue to be shaped or tailored as desired. Groupings of electrodes may be electrically connected to form larger or smaller effective stimulation areas. Individual or grouped electrodes may be independently controlled to provide varying levels of stimulation so as to shape activation fields to location or depth to preferentially activate underlying tissue, or to avoid or suppress activation of underlying tissue. In some examples, stimulation intensity can be adjusted to account for electrode position/proximity and/or side. For example, larger currents can be delivered with ganged-together electrodes with less concern regarding patient comfort. Also, varying frequencies of stimulation between electrodes may be used to activate, inhibit, or avoid stimulation of underlying tissue by creating interacting activation fields, like beat frequencies, or inferential therapy.

The circuitry in the stimulation device may include multiple outputs that allow for independent control over each electrode and/or plural electrode pairs, if desired, to allow multiple waveforms to be delivered at the same time. For example, a sinusoidal first stimulation signal issued between electrode 32*b* and electrode 46*b* at 40 Hz could be output at the same time as a second stimulation signal generated at 30 Hz using electrode 32*c* and electrode 46*c*, resulting in a 10 Hz beat frequency arising within the patient tissue. Other "beat" related approaches or interferential signals may be used instead or in addition to these examples.

Each of the non-limiting examples herein can stand on its own, or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described above. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A wearable device adapted for placement relative to an ear of a user, comprising:

a housing containing electronics and a power source;

a first extending structure having a first end at the housing and a second end apart from the housing, the first extending structure having a first length;

a second extending structure comprising a first end at the housing and a second end apart from the housing, wherein the first and second extending structures are separated by an adjustable distance, wherein the second extending structure is configured to abut a first inner portion of an ear to create an opposing force to the first extending structure which is configured to abut a second inner portion of the ear;

an anchor arm extending laterally from the first extending structure;

a carriage configured to move longitudinally along a length of the housing; and an adjustment mechanism configured to impart a force to cause longitudinal movement of the carriage to adjust the adjustable distance by longitudinally translating the second extending structure relative to the first extending structure.

2. The wearable device of claim 1, wherein the adjustment mechanism is an individual adjustment mechanism that is configured to be actuated by contact from one or more digits on an individual hand of a person.

3. The wearable device of claim 1, wherein:

the adjustment mechanism is located at a first end of the housing; and a portion of the adjustment mechanism extends a distance from the first end of the housing and a portion of the adjustment mechanism is located inside of the housing.

4. The wearable device of claim 1, wherein the first inner portion of the ear is the inferior crus, the antihelix, or both, and wherein the second inner portion of the ear is the antitragus.

5. The wearable device of claim 1, wherein the adjustment mechanism is integral with the carriage, wherein the carriage is coupled to the first end of the second extending structure.

6. The wearable device of claim 5, wherein the adjustment mechanism is located on a first end of the carriage, and wherein the adjustment mechanism comprises a protrusion extending radially from the carriage.

7. The wearable device of claim 1, wherein a speaker, a sensor, or both the speaker and the sensor are positioned on the first extending structure or the second extending structure.

8. The wearable device of claim 1, wherein the adjustment mechanism comprises a separate component that is coupled to the carriage, wherein the carriage is coupled to the first end of the second extending structure.

9. The wearable device of claim 8, wherein the adjustment mechanism further comprises a rotatable adjustment mechanism including an annulus, wherein the rotatable adjustment mechanism is configured to rotate about the annulus relative to the carriage, the housing, or both the carriage and the housing.

10. The wearable device of claim 9, wherein:

the housing includes a slot extending through the first end of the housing;

the rotatable adjustment mechanism comprises:

a lever extending laterally therefrom through the slot to a position outside of the housing; and teeth disposed along at least a portion of a periphery of the rotatable adjustment mechanism that is located in the housing; and the carriage includes corresponding teeth that are configured to interface with the teeth to impart the longitudinal movement of the carriage responsive to rotation of the lever.

11. The wearable device of claim 10, wherein:

the carriage includes an elongated longitudinal slot extending along a portion of the length of the carriage; and the housing includes a peg configured to extend into the elongated longitudinal slot.

12. The wearable device of claim 9, wherein:

the housing includes a slot extending through the first end of the housing; and the rotatable adjustment mechanism comprises a wheel with a toothed surface along at least a portion of a periphery of the rotatable adjustment mechanism and a curvilinear slot extending within a portion of the wheel.

13. The wearable device of claim 1, wherein an electrode is positioned on the first extending structure or the second extending structure.

14. The wearable device of claim 1, wherein a first electrode is positioned on the first extending structure and a second electrode is positioned on the second extending structure.

15. The wearable device of claim 14, wherein:

the first electrode and the second electrode are configured to be positioned on opposing sides of the crus helix; or the first electrode is configured to be positioned at the conchae caverna and the second electrode is configured to be positioned at the conchae cymba.

16. A wearable device adapted for placement relative to an ear of a user, comprising:

a housing containing electronics and a power source, wherein the housing comprises a lower container and an upper lid defining a cavity therebetween;

a first extending structure having a first end at the housing and a second end apart from the housing, the first extending structure having a first length;

an anchor arm extending laterally from the first extending structure;

a second extending structure comprising a first end at the housing and a second end apart from the housing, wherein the first and second extending structures are separated by an adjustable distance, wherein the second extending structure is configured to abut a first inner portion of an ear to create an opposing force to the first extending structure which is configured to abut a second inner portion of the ear;

a carriage coupled to the first end of the second extending structure and being at least partially disposed within the cavity of the housing, wherein the carriage is configured to translate longitudinally along a portion of a length of the housing;

an adjustment mechanism coupled to the carriage, wherein the adjustment mechanism is an individual adjustment mechanism that is configured to impart a force to cause longitudinal translation of the carriage to adjust the adjustable distance by longitudinally translating the second extending structure relative to the first extending structure; and an electrode, a vibrating element, or both, wherein the electrode, the vibrating element or both, is positioned on the first extending structure, the second extending structure, or both the first extending structure and the second extending structure.

17. The wearable device of claim 16, wherein:

the adjustment mechanism comprises a fixed protrusion extending radially from the carriage or a rotatable adjustment mechanism coupled to an end of the carriage; or the carriage, the housing, or both the carriage and the housing include detents configured to predispose the carriage to one or more longitudinal positions along a length of travel of the carriage.

18. The wearable device of claim 16, wherein the first extending structure or the second extending structure is integral with the housing.

19. The wearable device of claim 16, wherein:

the first inner portion of the ear is the inferior crus, the antihelix, or both, and wherein the second inner portion of the ear is the antitragus;

the wearable device includes the electrode, and the electrode includes a first electrode is positioned on the first extending structure and a second electrode is positioned on the second extending structure.

20. The wearable device of claim 16, wherein the electronics comprise wireless communication circuitry configured to wirelessly communicate with a mobile device application, wherein the mobile device application is configured to remotely control electrical stimulation parameters delivered via the electrode, the vibrating element, or both.

21. A method of treating inflammation in a patient, the method comprising:

applying a wearable device to an ear of the patient, the wearable device comprising a housing containing electronics, one or more electrodes, and a power source, a first extending structure having a second end positioned within the ear when the wearable device is worn, an anchor arm extending laterally from the first extending structure, a second extending structure having a second end positioned within the ear when the wearable device is worn, a carriage coupled to a first end of the second extending structure and being at least partially disposed within the housing, wherein the carriage is configured to move longitudinally along a length of the housing, and an adjustment mechanism coupled to the carriage, wherein the adjustment mechanism is configured to impart a force to cause longitudinal movement of the carriage to adjust a distance between the first extending structure and the second extending structure by longitudinally translating the second extending structure relative to the first extending structure; and delivering electrical stimulation via the one or more electrodes of the wearable device to activate a neuro-immune anti-inflammatory pathway in the patient to treat the inflammation.

22. The method of claim 21, wherein the applying further comprises placing the anchor arm in the ear of the user, and wherein the method further comprises actuating the adjustment mechanism to vary an adjustable distance between the first extending structure and the second extending structure to secure the wearable device to the ear of the patient.

23. The method of claim 22, wherein actuating the adjustment mechanism further comprises actuating the adjustment mechanism with one or more digits of an individual hand of a user subsequent to placing the anchor arm in the ear of the user until the second extending structure abuts the helix, the antihelix, the inferior crus, or any combination thereof.

24. The method of claim 21, further comprising delivering the electrical stimulation at a current amplitude in a range of about 0.1 mA to about 20 mA, a pulse width in a range of about 10 microseconds to about 20 milliseconds, and a frequency in a range of about 1 Hz to about 200 Hz.

25. The method of claim 21, wherein the inflammation is associated with one or more conditions selected from the group consisting of: cerebrovascular disorders including stroke and post-stroke inflammatory response; metabolic disorders including diabetes mellitus and glycemic control disorders; drug-induced inflammatory responses including diabetes drug therapy complications; rheumatoid arthritis; inflammatory bowel disease; Alzheimer's disease, Crohn's disease; ulcerative colitis; multiple sclerosis; psoriatic arthritis; osteoarthritis; psoriasis; chronic inflammatory symptoms; and chronic fatigue syndrome.

26. A wearable device adapted for placement relative to an ear of a user, comprising:

a housing containing electronics and a power source;

a first extending structure having a first end at the housing and a second end apart from the housing, the first extending structure having a first length, the second end configured for contacting the posterior edge of the crus and/or antitragus;

a first anchor arm extending laterally from the first extending structure and carrying an anchor element thereon, the anchor element configured for positioning beneath a tragus of the ear of the user to thereby support positioning of the wearable device;

a second extending structure comprising a first end at the housing and a second end apart from the housing, wherein the first and second extending structures are separated by an adjustable distance;

a carriage coupled to the first end of the second extending structure and being at least partially disposed within the housing, wherein the carriage is configured to move longitudinally along a length of the housing;

an adjustment mechanism coupled to the carriage, wherein the adjustment mechanism is configured to impart a force to cause longitudinal movement of the carriage to adjust the adjustable distance by longitudinally translating the second extending structure relative to the first extending structure; and an electrode, a vibrating element, or both, wherein the electrode, the vibrating element, or both, is located on the first extending structure, the second extending structure, or both.

27. The wearable device of claim 26, wherein the wearable device is configured to treat inflammation in the user.

28. The wearable device of claim 27, wherein the inflammation is associated with one or more conditions selected from the group consisting of: cerebrovascular disorders including stroke and post-stroke inflammatory response; metabolic disorders including diabetes mellitus and glycemic control disorders; drug-induced inflammatory responses including diabetes drug therapy complications; rheumatoid arthritis; inflammatory bowel disease; Alzheimer's disease, Crohn's disease; ulcerative colitis; multiple sclerosis; psoriatic arthritis; osteoarthritis; psoriasis; chronic inflammatory symptoms; and chronic fatigue syndrome.

29. The wearable device of claim 27, including the electrode on the first extending structure, the second extending structure, or both.

30. The wearable device of claim 27, including the vibrating element on the first extending structure, the second extending structure, or both.

* * * * *